US011213253B2

(12) United States Patent
Kassab et al.

(10) Patent No.: US 11,213,253 B2
(45) Date of Patent: Jan. 4, 2022

(54) LUMINAL ORGAN SIZING DEVICES AND METHODS

(71) Applicant: 3DT Holdings, LLC, San Diego, CA (US)

(72) Inventors: Ghassan S. Kassab, La Jolla, CA (US); Joanna Mleczko, San Diego, CA (US)

(73) Assignee: 3DT Holdings, LLC, San Diego, CA (US)

( * ) Notice: Subject to any disclaimer, the term of this patent is extended or adjusted under 35 U.S.C. 154(b) by 501 days.

(21) Appl. No.: 16/241,922

(22) Filed: Jan. 7, 2019

(65) Prior Publication Data

US 2019/0133528 A1 May 9, 2019

Related U.S. Application Data

(60) Continuation-in-part of application No. 16/011,007, filed on Jun. 18, 2018, which is a continuation-in-part (Continued)

(51) Int. Cl.
| | |
|---|---|
| *A61B 5/00* | (2006.01) |
| *A61F 2/24* | (2006.01) |
| *A61B 5/0538* | (2021.01) |
| *A61B 5/107* | (2006.01) |
| *A61B 5/053* | (2021.01) |
| *A61B 17/12* | (2006.01) |
| *A61B 17/00* | (2006.01) |
| *A61B 18/00* | (2006.01) |
| *A61B 18/14* | (2006.01) |
| *A61B 90/00* | (2016.01) |

(52) U.S. Cl.
CPC ............ *A61B 5/6853* (2013.01); *A61B 5/053* (2013.01); *A61B 5/0538* (2013.01); *A61B 5/1076* (2013.01); *A61B 17/12136* (2013.01); *A61F 2/2433* (2013.01); *A61F 2/2496* (2013.01); *A61B 17/12122* (2013.01); *A61B 18/1492* (2013.01); *A61B 2017/00026* (2013.01); *A61B 2018/0022* (2013.01); *A61B 2018/0072* (2013.01); *A61B 2018/00345* (2013.01); *A61B 2018/00404* (2013.01); *A61B 2018/00434* (2013.01); *A61B 2018/00511* (2013.01); *A61B 2018/00577* (2013.01); *A61B 2018/00755* (2013.01); *A61B 2018/00875* (2013.01); *A61B 2090/061* (2016.02); *A61B 2218/002* (2013.01); *A61B 2218/007* (2013.01); *A61F 2/2418* (2013.01)

(58) Field of Classification Search
CPC ..... A61B 5/6853; A61B 5/053; A61B 5/1076; A61B 5/0538; A61F 2/2496; A61F 2/2433; A61F 2/2472; A61F 2/2442
See application file for complete search history.

(56) References Cited

U.S. PATENT DOCUMENTS

| | | | |
|---|---|---|---|
| 2010/0168836 A1* | 7/2010 | Kassab | ................ A61B 5/0538 623/1.11 |
| 2017/0196509 A1* | 7/2017 | Hunter | ................ A61B 5/0028 |

* cited by examiner

*Primary Examiner* — Devin B Henson
(74) *Attorney, Agent, or Firm* — William F. Ward

(57) ABSTRACT

Luminal organ sizing devices and methods. In a method of the present disclosure, the method includes performing a valve replacement procedure using a valve device positioned within a valve annulus or opening of a luminal organ while a system including a balloon configured for inflation is at least partially introduced into a luminal organ so that the balloon is adjacent to a valve annulus or opening.

15 Claims, 18 Drawing Sheets

Related U.S. Application Data of application No. 15/156,364, filed on May 17, 2016, which is a continuation-in-part of application No. 13/850,758, filed on Mar. 26, 2013, now Pat. No. 9,339,230, which is a continuation of application No. 12/706,677, filed on Feb. 16, 2010, now Pat. No. 8,406,867, which is a continuation-in-part of application No. 11/891,981, filed on Aug. 14, 2007, now Pat. No. 8,114,143, which is a division of application No. 10/782,149, filed on Feb. 19, 2004, now Pat. No. 7,454,244.

(60) Provisional application No. 62/627,525, filed on Feb. 7, 2018, provisional application No. 62/613,814, filed on Jan. 5, 2018, provisional application No. 62/521,024, filed on Jun. 16, 2017, provisional application No. 62/261,357, filed on Dec. 1, 2015, provisional application No. 60/502,139, filed on Sep. 11, 2003, provisional application No. 60/493,145, filed on Aug. 7, 2003, provisional application No. 60/449,266, filed on Feb. 21, 2003.

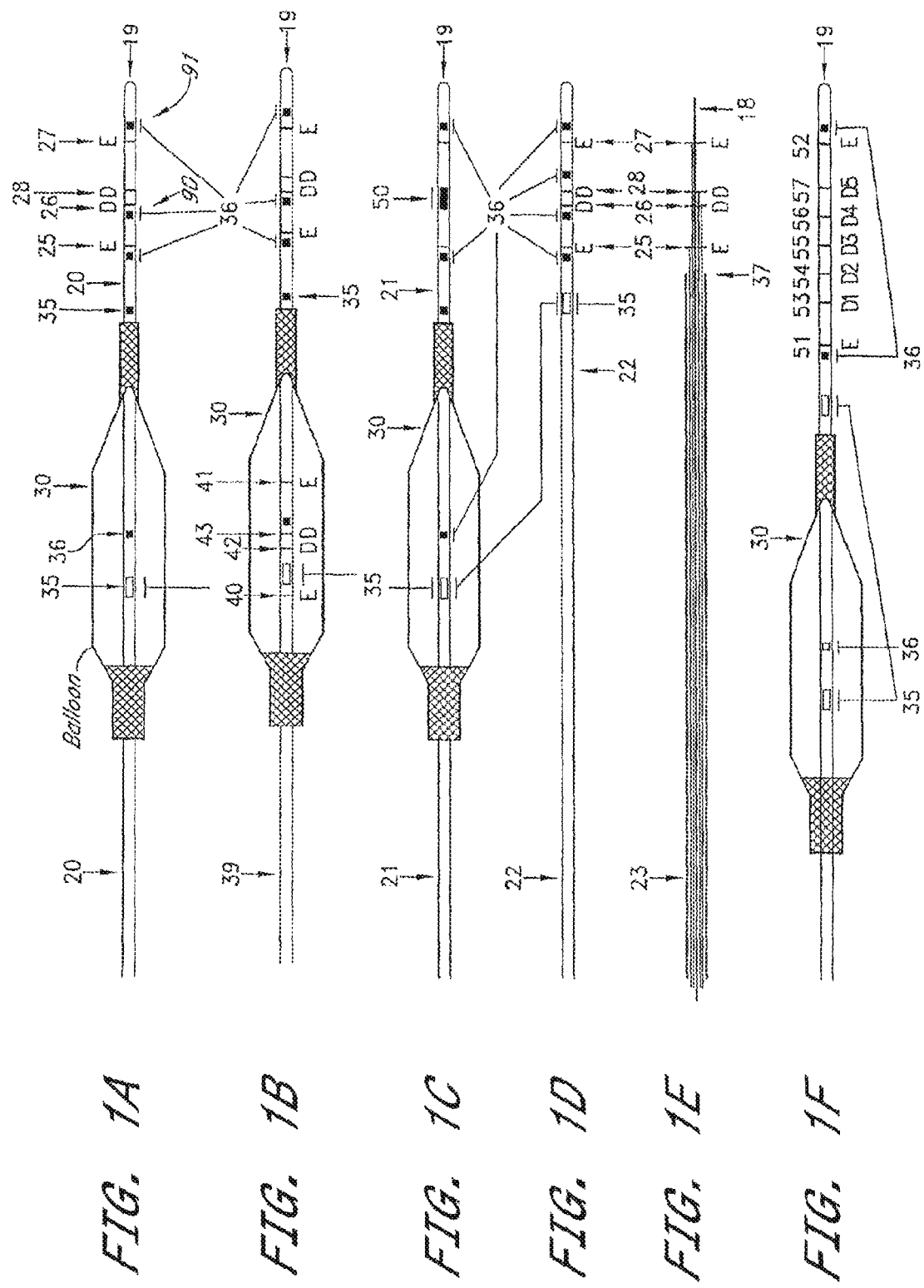

envelope data peak-peak of voltage at the detection electrodes

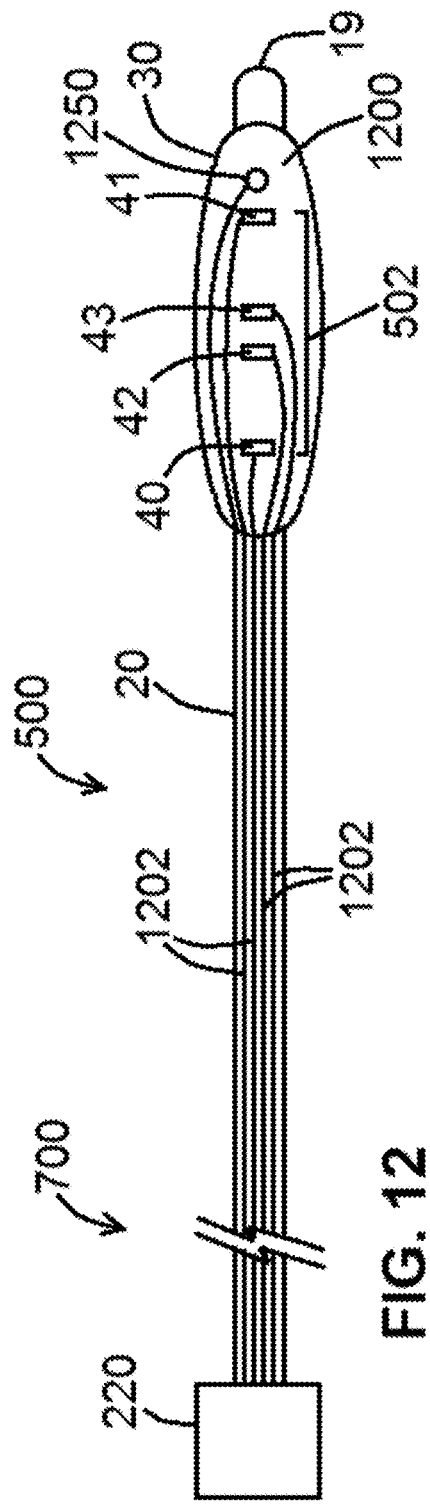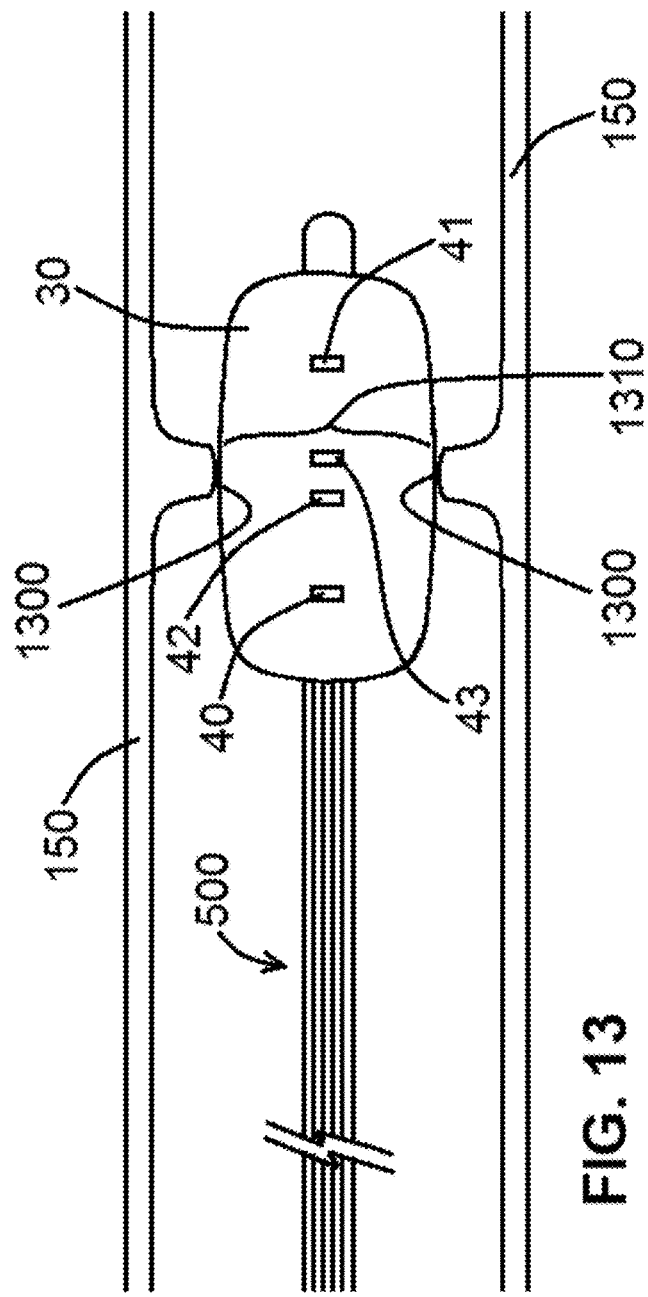

LUMINAL ORGAN SIZING DEVICES AND METHODS

RELATED APPLICATIONS

The present application is related to, and claims the priority benefit of, A) U.S. Provisional Patent Application Ser. No. 62/627,525, filed Feb. 7, 2018, and B) U.S. Provisional Patent Application Ser. No. 62/613,814, filed Jan. 5, 2018, and is related to, claims the priority benefit of, and is a U.S. continuation-in-part patent application of, U.S. patent application Ser. No. 16/011,007, filed Jun. 18, 2018, which i) is related to, claims the priority benefit of, U.S. Provisional Patent Application Ser. No. 62/521,024, filed Jun. 16, 2017, and ii) is related to, claims the priority benefit of, and is a U.S. continuation-in-part patent application of, U.S. patent application Ser. No. 15/156,364, filed May 17, 2016, which a) is related to, and claims the priority benefit of, Provisional Patent Application Ser. No. 62/261,357, filed Dec. 1, 2015, and b) is related to, claims the priority benefit of, and is a continuation-in-part application of, U.S. patent application Ser. No. 13/850,758, filed Mar. 26, 2013 and issued as U.S. Pat. No. 9,339,230 on May 17, 2016, which is related to, claims the priority benefit of, and is a continuation application of, U.S. patent application Ser. No. 12/706,677, filed Feb. 16, 2010 and issued as U.S. Pat. No. 8,406,867 on Mar. 26, 2013, which is related to, claims the priority benefit of, and is a continuation-in-part application of, U.S. patent application Ser. No. 11/891,981, filed Aug. 14, 2007 and issued as U.S. Pat. No. 8,114,143 on Feb. 14, 2012, which is related to, claims the priority benefit of, and is a divisional application of, U.S. patent application Ser. No. 10/782,149, filed Feb. 19, 2004 and issued as U.S. Pat. No. 7,454,244 on Nov. 18, 2008, which is related to, and claims the priority benefit of, U.S. Provisional Patent Application Ser. No. 60/449,266, filed Feb. 21, 2003, U.S. Provisional Patent Application Ser. No. 60/493,145, filed Aug. 7, 2003, and U.S. Provisional Patent Application Ser. No. 60/502,139, filed Sep. 11, 2003. The contents of each of these applications and patents are hereby incorporated by reference in their entirety into this disclosure.

BACKGROUND

Coronary heart disease (CHD) is commonly caused by atherosclerotic narrowing of the coronary arteries and is likely to produce angina pectoris, heart attacks or a combination. CHD caused 466,101 deaths in the USA in 1997 and is one of the leading causes of death in America today. Approximately, 12 million people alive today have a history of heart attack, angina pectoris or both. The break down for males and females is 49% and 51%, respectively. This year, an estimated 1.1 million Americans will have a new or recurrent coronary attack, and more than 40% of the people experiencing these attacks will die as a result. About 225,000 people a year die of coronary attack without being hospitalized. These are sudden deaths caused by cardiac arrest, usually resulting from ventricular fibrillation. More than 400,000 Americans and 800,000 patients world-wide undergo a non-surgical coronary artery interventional procedure each year. Although only introduced in the 1990s, in some laboratories intra-coronary stents are used in 90% of these patients.

Stents increase minimal coronary lumen diameter to a greater degree than percutaneous transluminal coronary angioplasty (PTCA) alone according to the results of two randomized trials using the Palmaz-Schatz stent. These trials compared two initial treatment strategies: stenting alone and PTCA with "stent backup" if needed. In the STRESS trial, there was a significant difference in successful angiographic outcome in favor of stenting (96.1% vs. 89.6%).

Intravascular Ultrasound

Currently intravascular ultrasound is the method of choice to determine the true diameter of the diseased vessel in order to size the stent correctly. The term "vessel," as used herein, refers generally to any hollow, tubular, or luminal organ. The tomographic orientation of ultrasound enables visualization of the full 360° circumference of the vessel wall and permits direct measurements of lumen dimensions, including minimal and maximal diameter and cross-sectional area. Information from ultrasound is combined with that obtained by angiography. Because of the latticed characteristics of stents, radiographic contrast material can surround the stent, producing an angiographic appearance of a large lumen, even when the stent struts are not in full contact with the vessel wall. A large observational ultrasound study after angiographically guided stent deployment revealed an average residual plaque area of 51% in a comparison of minimal stent diameter with reference segment diameter, and incomplete wall apposition was frequently observed. In this cohort, additional balloon inflations resulted in a final average residual plaque area of 34%, even though the final angiographic percent stenosis was negative (20.7%). These investigators used ultrasound to guide deployment.

However, using intravascular ultrasound as mentioned above requires a first step of advancement of an ultrasound catheter and then withdrawal of the ultrasound catheter before coronary angioplasty thereby adding additional time to the stent procedure. Furthermore, it requires an ultrasound machine. This adds significant cost and time and more risk to the procedure.

Aortic Stenosis

Aortic Stenosis (AS) is one of the major reasons for valve replacements in adult. AS occurs when the aortic valve orifice narrows secondary to valve degeneration. The aortic valve area is reduced to one fourth of its normal size before it shows a hemodynamic effect. Because the area of the normal adult valve orifice is typically 3.0 to 4.0 $cm^2$, an area 0.75-1.0 $cm^2$ is usually not considered severe AS. When stenosis is severe and cardiac output is normal, the mean trans-valvular pressure gradient is generally >50 mmHg. Some patients with severe AS remain asymptomatic, whereas others with only moderate stenosis develop symptoms. Therapeutic decisions, particularly those related to corrective surgery, are based largely on the presence or absence of symptoms.

The natural history of AS in the adult consists of a prolonged latent period in which morbidity and mortality are very low. The rate of progression of the stenotic lesion has been estimated in a variety of hemodynamic studies performed largely in patients with moderate AS. Cardiac catheterization and Doppler echocardiographic studies indicate that some patients exhibit a decrease in valve area of 0.1-0.3 $cm^2$ per year; the average rate of change is 0.12 $cm^2$ per year. The systolic pressure gradient across the valve may increase by as much as 10 to 15 mmHg per year. However, more than half of the reported patients showed little or no progression over a 3-9 year period. Although it appears that progression of AS can be more rapid in patients with degenerative calcific disease than in those with congenital or rheumatic disease, it is not possible to predict the rate of progression in an individual patient.

Eventually, symptoms of angina, syncope, or heart failure develop after a long latent period, and the outlook changes dramatically. After onset of symptoms, average survival is <2-3 years. Thus, the development of symptoms identifies a critical point in the natural history of AS.

Many asymptomatic patients with severe AS develop symptoms within a few years and require surgery. The incidence of angina, dyspnea, or syncope in asymptomatic patients with Doppler outflow velocities of 4 m/s has been reported to be as high as 38% after 2 years and 79% after 3 years. Therefore, patients with severe AS require careful monitoring for development of symptoms and progressive disease.

Indications for Cardiac Catheterization

In patients with AS, the indications for cardiac catheterization and angiography are to assess the coronary circulation (to confirm the absence of coronary artery disease) and to confirm or clarify the clinical diagnosis of AS severity. If echocardiographic data are typical of severe isolated. AS, coronary angiography may be all that is needed before aortic valve replacement (AVR). Complete left- and right-heart catheterization may be necessary to assess the hemodynamic severity of AS if there is a discrepancy between clinical and echocardiographic data or evidence of associated valvular or congenital disease or pulmonary hypertension.

The pressure gradient across a stenotic valve is related to the valve orifice area and transvalvular flow through Bernoulli's principle. Thus, in the presence of depressed cardiac output, relatively low pressure gradients are frequently obtained in patients with severe AS. On the other hand, during exercise or other high-flow states, systolic gradients can be measured in minimally stenotic valves. For these reasons, complete assessment of AS requires (1) measurement of transvalvular flow, (2) determination of the transvalvular pressure gradient, and (3) calculation of the effective valve area. Careful attention to detail with accurate measurements of pressure and flow is important, especially in patients with low cardiac output or a low transvalvular pressure gradient.

Problems with Current Aortic Valve Area Measurements

Patients with severe AS and low cardiac output are often present with only modest transvalvular pressure gradients (i.e., <30 mmHg). Such patients can be difficult to distinguish from those with low cardiac output and only mild to moderate AS. In both situations, the low-flow state and low pressure gradient contribute to a calculated effective valve area that can meet criteria for severe AS. The standard valve area formula (simplified Hakki formula which is valve area=cardiac output/[pressure gradient]$^{1/2}$) is less accurate and is known to underestimate the valve area in low-flow states; under such conditions, it should be interpreted with caution. Although valve resistance is less sensitive to flow than valve area, resistance calculations have not been proved to be substantially better than valve area calculations.

In patients with low gradient stenosis and what appears to be moderate to severe AS, it may be useful to determine the transvalvular pressure gradient and calculate valve area and resistance during a baseline state and again during exercise or pharmacological (i.e., dobutamine infusion) stress. Patients who do not have true, anatomically severe stenosis exhibit an increase in the valve area during an increase in cardiac output. In patients with severe AS, these changes may result in a calculated valve area that is higher than the baseline calculation but that remains in the severe range, whereas in patients without severe AS, the calculated valve area will fall outside the severe range with administration of dobutamine and indicate that severe AS is not present.

There are many other limitations in estimating aortic valve area in patients with aortic stenosis using echocardiography and cardiac catheterization. Accurate measurement of the aortic valve area in patients with aortic stenosis can be difficult in the setting of low cardiac output or concomitant aortic or mitral regurgitations. Concomitant aortic regurgitation or low cardiac output can overestimate the severity of aortic stenosis. Furthermore, because of the dependence of aortic valve area calculation on cardiac output, any under or overestimation of cardiac output will cause inaccurate measurement of valve area. This is particularly important in patients with tricuspid regurgitation. Falsely measured aortic valve area could cause inappropriate aortic valve surgery in patients who do not need it.

Other Visceral Organs

Visceral organs such as the gastrointestinal tract and the urinary tract serve to transport luminal contents (fluids) from one end of the organ to the other end or to an absorption site. The esophagus, for example, transports swallowed material from the pharynx to the stomach. Diseases may affect the transport function of the organs by changing the luminal cross-sectional area, the peristalsis generated by muscle, or by changing the tissue components. For example, strictures in the esophagus and urethra constitute a narrowing of the organ where fibrosis of the wall may occur. Strictures and narrowing can be treated with distension, much like the treatment of plaques in the coronary arteries.

Valve Sizing and Replacement

In addition, percutaneous interventional therapy has been an option for patients with pulmonic, mitral, and aortic valvular disease for decades. The treatment preferred in selected patients with pulmonic or mitral stenosis is percutaneous valvuloplasty. According to the current ACC/American Heart Association (AHA) guidelines, in patients with calcific aortic stenosis, balloon aortic valvuloplasty (BAV) has been used as a bridge to aortic valve replacement.

Hospital mortality for BAV varies from 3.5% to 13.5%, while serious complications appear in at least 25% of the patients. The durability of BAV is restricted. Consequently, open aortic valve replacement continues to be the best therapy for aortic stenosis (AS) in patients who are viable candidates for surgery. The most frequent heart valve operation is the aortic valve replacement. In the United States, from 2% to 7% of individuals older than 65 years suffer from AS, which will continue to increase as more people live longer. AS is frequently associated with comorbid risk factors and previous bypass surgery since it is persistently progressive and it takes place in elderly patients. The surgical therapy for AS patients is useful to improve symptoms and prolong life.

Percutaneous strategies for the treatment of AS began with percutaneous balloon valvuloplasty. Data from the multicenter National Heart, Lung, and Blood Institute (NHLBI) registry, however, showed only a mild progress in early hemodynamics, a significant incidence of peripheral vascular complications, a 30 day mortality of 7%, and a high incidence of restenosis within 6 months.

The unsatisfactory BAV results have led to the investigation of percutaneous placement of prosthetic aortic valves. Devices to perform the same have been clinically utilized in a small number of cases in high-risk patients. Although percutaneous aortic valve insertion has been performed on extremely high-risk patients, considerable para-valvular leak regurgitation and early mortality discourage the approach.

One concern with percutaneous or transapical aortic valve replacement is the sizing of dilatation of the calcific aortic valve prior to delivery of the stent valve device. The consequences of incorrect sizing of the aortic valve area are periprosthetic leak, calcium embolization, and difficulties in the insertion of the device and its possible migration.

Ischemic mitral regurgitation (IMR) is a mitral valve insufficiency that is produced by acute myocardial infarction (AMI) and later infarction-induced left ventricular remodeling. Approximately 1.2 to 2.1 million patients in the United States suffer IMR, including more than 400,000 patients running moderate-to-severe MR. It is estimated that about 50-60% of congestive heart failure (CHF) patients suffer from some type of mitral regurgitation (MR). The valve is structurally normal in the vast majority of these patients.

In end-stage heart failure patient, the mechanism of MR is multifactorial and it is related to changes in left ventricular (LV) geometry, with a subsequent displacement of the subvalvular apparatus, annular dilatation, and restrictive leaflet motion, which ends in failure of the leaflet coaptation. Physiologically, IMR in these patients will lead to LV overload and decrease of stroke volume.

Numerous investigators support the use of a stringent restrictive ring (which is two sizes smaller than the measured size) in order to obtain better leaflet coaptation. This avoids MR recurrence and promotes reverse remodeling. Midterm follow-up (18 months) with this approach shows reverse remodeling in 58% of patients. During direct visualization in surgery, the sizing of the annulus can be accurately determined and made appropriate for each patient.

Patients with MR have a considerably diminished survival at 2 years' follow-up versus patients lacking mitral regurgitation. Furthermore, the severity of mitral regurgitation is directly associated to mortality risk. The undersizing of the mitral annulus will lead to acute valuable geometric changes of the base of the left ventricle, which might diminish LV volume and wall stress. When mitral regurgitation is treated conservatively morbidity and mortality is high.

It seems logical to correct mitral regurgitation in patients with end-stage heart failure (HF) in order to improve prognosis. However, and at the present time, mitral annuloplasty is not routinely performed in these patients due to significant mortality and elevated recurrence rates. On the other hand, numerous recent investigations have demonstrated somewhat low operative mortality suggesting improved long-term survival after stringent restrictive mitral annuloplasty.

Surgical approaches to MR include mitral valve replacement and repair, with the latest studies supporting early repair in structural MR when possible or in patients with ischemic MR and symptomatic HF but morbidity, mortality, and late recurrent mitral regurgitation limit extensive surgical repair application. Surgical mitral repair could be sophisticated and complex, but the majority of repairs currently consist of simple annuloplasty.

Recently, percutaneous approaches to mitral annuloplasty as well as percutaneous replacement of mitral valve have been shown to reduce MR of global left ventricular dysfunction, acute ischemia, and chronic post-infarction. A number of devices have been described to remodel or replace the mitral annulus to decrease annular anteroposterior diameter.

The possibility of balloon sizing of valve annulus prior to committing to a particular size valve is essential. Furthermore, the sizing of the stent valve during delivery will ensure good apposition and prevent leak, migration or erosion over the long term.

Thus, a need exists in the art for an alternative to the conventional devices and methods for sizing a valve annulus for the subsequent replacement of mitral valves, for example. A further need exists for a reliable, accurate and minimally invasive system or technique of sizing a percutaneous valve and/or a valve annulus and positioning a stent valve therein.

Furthermore, and by the year 2030, 20% of the American population will be of age 65 and older, elevating the number of patients at high risk of suffering from valvular heart disease to above 70 million. While Aortic stenosis (AS) affects approximately 1.5M Americans, mitral valve (MV) disease accounts for 60% of all valvular diseases, most frequently mitral regurgitation (MR) which alone affects 7.8 million patients. If left untreated, valvular disease leads to left ventricular (LV) dysfunction/remodeling, reductions in coronary blood flow, heart failure (HF), and eventually death. While transcatheter aortic valve replacement (TAVR) is becoming the new standard (over the surgical approach), the mitral valve is most frequently replaced surgically, leaving no treatment options for patients rejected from surgery.

Due mainly to high perioperative mortality risk, about 50% of severe mitral stenosis patients never receive surgery, while high risk MR patients only qualify for Mitral clip. As a result, percutaneous catheter delivery of a prosthetic mitral valve, called transcatheter mitral valve replacement (TMVR), is emerging as a treatment option for severe MV disease. Compassionate use applications of TAVR valves in MR patients show promising results for high surgical risk patients in need of a new MV. The FDA has recently approved Edwards Lifesciences Sapien 3 for usage as a transcatheter mitral valve for U.S. in both inoperable and high-risk surgical MR patients. While paravalvular leakage used to be a main concern in patients following TAVR, left ventricular outflow tract (LVOT) obstruction and annular rupture remain the biggest concerns in TMVR. Currently, both multi-detector computed tomography (MDCT), transesophageal echocardiography (TEE) and 3-D printing of the native valve based on patient data are used to determine mitral annulus size prior to TMVR, but these imaging modalities rely on subjective image interpretation for sizing, and are non-dynamic or real time.

Therefore, a new device, method and system that would add no procedural time or cost and produces accurate mitral annular sizing measurements and/or a diagnostic feature of LVOT obstruction during the TMVR implant procedure would be well received.

BRIEF SUMMARY

In at least one embodiment of a method to size a valve annulus of the present disclosure, the method comprises the steps of introducing at least part of a sizing device into a luminal organ at a valve annulus, the sizing device having a detector and a pressure transducer within a balloon positioned at or near a distal end of the detection device, inflating the balloon until a threshold pressure is detected by the pressure transducer within the balloon, obtaining a first valve annulus measurement using the detector, and withdrawing the sizing device from the luminal organ. In another embodiment, the method further comprises the steps of positioning a stent valve upon the balloon, reintroducing at least part of a sizing device into the luminal organ at the valve annulus, and reinflating the balloon to the first valve annulus measurement to place the stent valve within the valve annulus. In yet another embodiment, the method further comprises the step of rewithdrawing the sizing device from the luminal organ.

In at least one embodiment of a method to size a valve annulus of the present disclosure, the sizing device further comprises a catheter having a lumen therethrough and defining a suction/infusion port within the catheter within the balloon. In an additional embodiment, the step of inflating the balloon comprises introducing a fluid into the lumen of the catheter, through the suction/infusion port, and into the balloon. In another embodiment, the step of withdrawing the sizing device comprises removing fluid from the balloon, through the suction/infusion port, and into the lumen of the catheter, to deflate the balloon. In yet another embodiment, the detector comprises two detection electrodes positioned in between two excitation electrodes, the excitation electrodes capable of producing an electric field to facilitate a conductance measurement of a fluid within the balloon. In an additional embodiment, the step obtaining a first valve annulus measurement comprises obtaining a balloon cross sectional area using the detector.

In at least one embodiment of a method to size a valve annulus of the present disclosure, the step of obtaining a first valve annulus measurement comprises measuring a balloon cross-sectional area using the detector when the threshold pressure is present within the balloon. In another embodiment, the balloon cross-sectional area is determined from a conductance measurement of a fluid present within the balloon obtained by the detector, a known conductivity of the fluid, and a known distance between two detection electrodes of the detector.

In at least one embodiment of a method to size a valve annulus of the present disclosure, the step of inflating the balloon comprises injecting a solution having a known conductivity into the balloon. In another embodiment, the step of obtaining a first valve annulus measurement comprises measuring a cross-sectional area based in part of the conductivity of the fluid and a conductance value obtained using the detector.

In at least one embodiment of a device to size a valve annulus of the present disclosure, the device comprises an elongated body extending from a proximal end to a distal end and having a lumen therethrough, a balloon positioned along the elongated body at or near the distal end, a detector and a pressure transducer positioned along the elongated body within the balloon, and a suction/infusion port defined within the elongated body within the balloon.

In at least one embodiment, the detector comprises a pair of excitation electrodes located on the elongated body, and a pair of detection electrodes located on the elongated body in between the pair of excitation electrodes, wherein the detector is capable of obtaining a conductance measurement of a fluid within the balloon. In another embodiment, the pair of excitation electrodes are capable of producing an electrical field, and wherein the pair of detection electrodes are capable of measuring an conductance of the fluid within the balloon. In an additional embodiment, at least one excitation electrode of the pair of excitation electrodes is/are in communication with a current source capable of supplying electrical current to the at least one excitation electrode.

In at least one embodiment of a device to size a valve annulus of the present disclosure, the device further comprises a data acquisition and processing system capable of receiving conductance data from the pair of detection electrodes. In an additional embodiment, the data acquisition and processing system is further capable of calculating a first valve annulus measurement within the balloon based from the conductance measurement of the fluid within the balloon obtained by the detector, a known conductivity of the fluid, and a known distance between the pair of detection electrodes. In another embodiment, the pressure transducer is capable of detecting a pressure within the balloon. In yet another embodiment, the suction/infusion port is in communication with the lumen of the elongated body, thereby enabling injection of a solution into the lumen of the elongated body, through the suction/infusion port, and into the balloon. In various embodiments, the lumen of the elongated body is in communication with a source of a solution to be injected therethrough and through the suction/infusion port into the balloon. In an additional embodiment, when a fluid is injected through the lumen of the elongated body into the balloon, the detector is capable of obtaining a fluid conductance measurement within the balloon, wherein the fluid conductance measurement is useful to determine balloon cross-sectional area.

In at least one embodiment of a system to size a valve annulus of the present disclosure, the system comprises a device comprising an elongated body extending from a proximal end to a distal end and having a lumen therethrough, a balloon positioned along the elongated body at or near the distal end, a detector and a pressure transducer positioned along the elongated body within the balloon, and a suction/infusion port defined within the elongated body within the balloon, the system also comprising a current source coupled to the detector and the pressure transducer, and a data acquisition and processing system capable of receiving conductance data from the detector and calculating a balloon cross-sectional area based upon a detected conductance of a fluid within the balloon from the detector, a known conductivity of the fluid, and a known distance between two detection electrodes of the detector.

In at least one embodiment of a method of the present disclosure, the method comprises the steps of introducing at least part of a first device into a luminal organ at an aperture or opening of the luminal organ, the first device having a balloon positioned thereon; inflating the balloon at the aperture or opening of the luminal organ until a point of apposition is achieved; and obtaining a first aperture or opening measurement based upon the point of apposition. In at least one embodiment of a method of the present disclosure, the first device is configured as a catheter having a lumen therethrough and defining a suction/infusion port so that the lumen is in communication with the balloon, and wherein the step of inflating is performed by introducing a fluid through the lumen, through the suction/infusion port, and into the balloon.

In at least one embodiment of a method of the present disclosure, the first device further comprises at least one electrode positioned within the balloon, and the step of obtaining the first aperture or opening measurement is performed by obtaining a size measurement within the balloon using the electrode. In at least one embodiment of a method of the present disclosure, conductance data is obtained at various stages of balloon inflation during the inflating step. In at least one embodiment of a method of the present disclosure, the method further comprises the step of operating an ablation contact positioned upon or within a surface of the balloon while the balloon is in contact with the luminal organ to ablate the luminal organ. In at least one embodiment of a method of the present disclosure, the luminal organ comprises a renal artery, and wherein the method is performed to treat hypertension.

In at least one embodiment of a method of the present disclosure, the method further comprises the step of determining various size measurements of the balloon corresponding to the conductance data obtained at the various stages of balloon inflation. In at least one embodiment of a method of the present disclosure, the method further comprises the step of determining compliance of the luminal organ at the opening or aperture based upon the various size measurements. In at least one embodiment of a method of the present disclosure, the opening or aperture is a septum of a heart, and wherein the determining step is performed to determine compliance of the septum of the heart. In at least one embodiment of a method of the present disclosure, the method further comprises the step of treating an intraseptal ventricular defect based upon the determined compliance of the luminal organ.

In at least one embodiment of a method of the present disclosure, the method comprises the steps of introducing at least part of a first device into a luminal organ so that a balloon of the first device is positioned at an aperture or opening of the luminal organ; inflating the balloon at the aperture or opening and obtaining conductance data within the balloon at various stages of balloon inflation using a detector positioned within the balloon; determining various size measurements of the balloon corresponding to the conductance data obtained at the various stages of balloon inflation; and determining compliance of the luminal organ at the aperture or opening based upon the various size measurements. In at least one embodiment of a method of the present disclosure, the step of inflating is performed to inflate the balloon so that the balloon contacts the luminal organ at the aperture or opening and to obtain conductance data at various stages of balloon prior to the balloon contacting the luminal organ at the aperture or opening and after the balloon contacts the luminal organ at the aperture or opening.

In at least one embodiment of a method of the present disclosure, compliance of the luminal organ is determined as being rigid or relatively rigid based upon at least some of the various size measurements corresponding to conductance data obtained after the balloon contacts the luminal organ at the aperture or opening being consistent with one another.

In at least one embodiment of a method of the present disclosure, compliance of the luminal organ is determined as being compliant or relatively compliant based upon an increase in the various size measurements corresponding to conductance data obtained after the balloon contacts the luminal organ at the aperture or opening being consistent with one another. In at least one embodiment of a method of the present disclosure, compliance of the luminal organ is determined as being rigid or relatively right based upon a lack of change in the various size measurements corresponding to conductance data obtained after the balloon contacts the luminal organ at the aperture or opening.

In at least one embodiment of a method of the present disclosure, the method further comprises the step of operating an ablation contact positioned upon or within a surface of the balloon while the balloon is in contact with the luminal organ to ablate the luminal organ. In at least one embodiment of a method of the present disclosure, the luminal organ comprises a renal artery, and wherein the method is performed to treat hypertension.

In at least one embodiment of a method of the present disclosure, the method comprises the steps of introducing at least part of a first device into a luminal organ so that a balloon of the first device is positioned at an aperture or opening of the luminal organ; first inflating the balloon at the aperture or opening and obtaining first conductance data within the balloon at various stages of balloon inflation until the balloon contacts the luminal organ at the aperture or opening; second inflating the balloon at the aperture or opening and obtaining second conductance data within the balloon at various stages of balloon inflation after the balloon contacts the luminal organ at the aperture or opening; determining various size measurements of the balloon corresponding to the second conductance data; and determining compliance of the luminal organ at the aperture or opening based upon the various size measurements. In at least one embodiment of a method of the present disclosure, compliance of the luminal organ is determined as being compliant or relatively compliant based upon an increase in the various size measurements corresponding to the second conductance data. In at least one embodiment of a method of the present disclosure, compliance of the luminal organ is determined as being rigid or relatively right based upon a lack of change in the various size measurements corresponding to the second conductance data.

In at least one embodiment of a method of the present disclosure, the method comprises the steps of introducing at least part of a first device into a luminal organ at an aperture or opening of the luminal organ at an atrial appendage (referring to the opening of the atrial appendage itself), the first device having a balloon positioned thereon; inflating the balloon at the aperture or opening until a point of apposition is achieved; and obtaining a first aperture or opening measurement based upon the point of apposition.

In at least one embodiment of a method of the present disclosure, the first device is configured as a catheter having a lumen therethrough and defining a suction/infusion port so that the lumen is in communication with the balloon, and wherein the step of inflating is performed by introducing a fluid through the lumen, through the suction/infusion port, and into the balloon.

In at least one embodiment of a method of the present disclosure, the first device further comprises at least one electrode positioned within the balloon, and wherein the step of obtaining the first aperture or opening measurement is performed by obtaining a size measurement within the balloon using the electrode.

In at least one embodiment of a method of the present disclosure, conductance data is obtained at various stages of balloon inflation during the inflating step.

In at least one embodiment of a method of the present disclosure, the method further comprises the step of operating an ablation contact positioned upon or within a surface of the balloon while the balloon is in contact with the luminal organ to ablate the luminal organ.

In at least one embodiment of a method of the present disclosure, the method further comprises the step of determining various size measurements of the balloon corresponding to the conductance data obtained at the various stages of balloon inflation.

In at least one embodiment of a method of the present disclosure, the method further comprises the step of determining compliance of the luminal organ at the opening or aperture based upon the various size measurements.

In at least one embodiment of a method of the present disclosure, the method further comprises the step of treating a defect based upon the determined compliance of the luminal organ.

In at least one embodiment of a method of the present disclosure, the atrial appendage comprises a left atrial appendage or a right atrial appendage.

In at least one embodiment of a method of the present disclosure, the method further comprises the step of selecting an appropriately sized occluder to occlude the opening of the atrial appendage or the atrial appendage itself based upon the first aperture or opening measurement obtained using the first device or based upon the various size measurements, as applicable.

In at least one embodiment of a method of the present disclosure, the method comprises the steps of introducing at least part of a first device into a luminal organ so that a balloon of the first device is positioned at an aperture or opening of the luminal organ at an atrial appendage (referring to the opening of the atrial appendage itself); inflating the balloon at the aperture or opening and obtaining conductance data within the balloon at various stages of balloon inflation using a detector positioned within the balloon; and determining various size measurements of the balloon corresponding to the conductance data obtained at the various stages of balloon inflation.

In at least one embodiment of a method of the present disclosure, the method further comprises the step of determining compliance of the luminal organ at the aperture or opening based upon the various size measurements.

In at least one embodiment of a method of the present disclosure, the step of inflating is performed to inflate the balloon so that the balloon contacts the luminal organ at the aperture or opening and to obtain conductance data at various stages of balloon prior to the balloon contacting the luminal organ at the aperture or opening and after the balloon contacts the luminal organ at the aperture or opening.

In at least one embodiment of a method of the present disclosure, compliance of the luminal organ is determined as being rigid or relatively rigid based upon at least some of the various size measurements corresponding to conductance data obtained after the balloon contacts the luminal organ at the aperture or opening being consistent with one another.

In at least one embodiment of a method of the present disclosure, compliance of the luminal organ is determined as being compliant or relatively compliant based upon an increase in the various size measurements corresponding to conductance data obtained after the balloon contacts the luminal organ at the aperture or opening being consistent with one another.

In at least one embodiment of a method of the present disclosure, compliance of the luminal organ is determined as being rigid or relatively right based upon a lack of change in the various size measurements corresponding to conductance data obtained after the balloon contacts the luminal organ at the aperture or opening.

In at least one embodiment of a method of the present disclosure, the method further comprises the step of operating an ablation contact positioned upon or within a surface of the balloon while the balloon is in contact with the luminal organ to ablate the luminal organ.

In at least one embodiment of a method of the present disclosure, the luminal organ comprises a renal artery, and wherein the method is performed to treat hypertension.

In at least one embodiment of a method of the present disclosure, the method comprises the steps of introducing at least part of a first device into a luminal organ so that a balloon of the first device is positioned at an aperture or opening of the luminal organ at an atrial appendage (referring to the opening of the atrial appendage itself); first inflating the balloon at the aperture or opening and obtaining first conductance data within the balloon at various stages of balloon inflation until the balloon contacts the luminal organ at the aperture or opening; second inflating the balloon at the aperture or opening and obtaining second conductance data within the balloon at various stages of balloon inflation after the balloon contacts the luminal organ at the aperture or opening; and determining various size measurements of the balloon corresponding to the second conductance data.

In at least one embodiment of a method of the present disclosure, the method further comprises the step of determining compliance of the luminal organ at the aperture or opening based upon the various size measurements.

In at least one embodiment of a method of the present disclosure, compliance of the luminal organ is determined as being compliant or relatively compliant based upon an increase in the various size measurements corresponding to the second conductance data.

In at least one embodiment of a method of the present disclosure, compliance of the luminal organ is determined as being rigid or relatively right based upon a lack of change in the various size measurements corresponding to the second conductance data.

In at least one embodiment of a method of the present disclosure, the method further comprises the step of selecting an appropriately sized occluder to occlude the opening of the atrial appendage or the atrial appendage itself based upon the various size measurements.

In at least one embodiment of a method of the present disclosure, the method comprises the steps of introducing at least part of a first device into an atrial appendage so that a balloon of the first device is positioned within the atrial appendage; inflating the balloon within the atrial appendage and obtaining conductance data within the balloon at various stages of balloon inflation using a detector positioned within the balloon; determining various size measurements of the balloon corresponding to the conductance data obtained at the various stages of balloon inflation.

In at least one embodiment of a method of the present disclosure, the method further comprises the step of determining compliance of the atrial appendage based upon the various size measurements.

In at least one embodiment of a method of the present disclosure, the method further comprises the step of selecting an appropriately sized occluder to occlude the atrial appendage based upon the various size measurements.

In at least one embodiment of a method of the present disclosure, the method comprises introducing at least part of a system comprising a balloon configured for inflation into a luminal organ so that the balloon is adjacent to a valve annulus or opening; introducing a valve device within the valve annulus or opening, adjacent the balloon; moving the valve device within the valve annulus or opening; operating the system to obtain measurements of the balloon over time during the step of moving the valve device within the valve annulus or opening; and generating a real-time measurement profile of the measurements over time.

In at least one embodiment of a method of the present disclosure, the method is performed to assess left ventricular outflow tract (LVOT) reduction during a valve replacement procedure.

In at least one embodiment of a method of the present disclosure, the measurements are size measurements, and wherein the method is performed to produce accurate mitral annular sizing measurements.

In at least one embodiment of a method of the present disclosure, the method further comprises the step of obtaining at least one initial measurement of the balloon when adjacent to the valve annulus or opening prior to the step of introducing the valve device within the valve annulus or opening, the at least one initial measurement selected from the group consisting of an initial sizing measurement and an initial pressure measurement.

In at least one embodiment of a method of the present disclosure, the real-time measurement profile can indicate external pinching of the balloon from the valve device when the real-time measurement profile indicates a decrease in size of the balloon.

In at least one embodiment of a method of the present disclosure, an axis of fluid flow through the valve annulus or opening is defined as an optimal axis of flow, and wherein the step of moving the valve device is performed to align the device along and consistent with a perpendicular axis that is perpendicular to the axis of fluid flow, wherein the perpendicular axis corresponds to an axis of the valve annulus or opening.

In at least one embodiment of a method of the present disclosure, when the step of moving the valve device causes an increase in pressure within the balloon, which is indicative of improper alignment of the valve device within the valve annulus or opening.

In at least one embodiment of a method of the present disclosure, the measurements are pressure measurements, wherein when the step of moving the valve devices causes a change in pressure within the balloon, and wherein a relative lowest pressure within the balloon is indicative of proper alignment of the valve device within the valve annulus or opening.

In at least one embodiment of a method of the present disclosure, the real-time sizing profile corresponds to a degree of left ventricular outflow tract (LVOT) obstruction over time.

In at least one embodiment of a method of the present disclosure, the measurements comprise size measurements, the system further comprises at least two detection electrodes positioned in between two excitation electrodes, excitation of the two excitation electrodes permits impedance measurements to be obtained within the balloon, and the impedance measurements correspond to the size measurements.

In at least one embodiment of a method of the present disclosure, the increase in pressure is determined using a pressure sensor or pressure transducer positioned within the balloon.

In at least one embodiment of a method of the present disclosure, the measurements comprise pressure measurements, the real-time measurement profile comprises a real-time pressure measurement profile, the system further comprises a pressure sensor or pressure transducer positioned within the balloon, and the step of generating the real-time measurement profile is performed to generate the real-time pressure measurement profile.

In at least one embodiment of a method of the present disclosure, the system further comprises at least two detection electrodes positioned in between two excitation electrodes, the system does not comprise a pressure sensor or pressure transducer, and the step of operating the system is performed to obtain the measurements corresponding to size measurements of the balloon over time.

In at least one embodiment of a method of the present disclosure, the system further comprises a pressure sensor or pressure transducer positioned within the balloon, the system does not comprise any excitation electrodes or any detection electrodes, and the step of operating the system is performed to obtain the measurements corresponding to pressure measurements within the balloon over time.

In at least one embodiment of a method of the present disclosure, the system further comprises at least two detection electrodes positioned in between two excitation electrodes, the system further comprises a pressure sensor or pressure transducer positioned within the balloon, and the step of operating the system is performed to obtain the measurements corresponding to size measurements of the balloon over time and pressure measurements within the balloon over time.

In at least one embodiment of a method of the present disclosure, the method comprises performing a valve replacement procedure using a valve device positioned within a valve annulus or opening of a luminal organ while a system comprising a balloon configured for inflation is at least partially introduced into a luminal organ so that the balloon is adjacent to a valve annulus or opening.

In at least one embodiment of a method of the present disclosure, the method further comprises operating the system to obtain measurements of the balloon over time during the valve replacement procedure; and generating a real-time measurement profile of the measurements over time.

BRIEF DESCRIPTION OF THE DRAWINGS

FIG. 1A shows a balloon catheter having impedance measuring electrodes supported in front of the stenting balloon, according to an embodiment of the present disclosure;

FIG. 1B shows a balloon catheter having impedance measuring electrodes within and in front of the balloon, according to an embodiment of the present disclosure;

FIG. 1C shows a catheter having an ultrasound transducer within and in front of balloon, according to an embodiment of the present disclosure;

FIG. 1D shows a catheter without a stenting balloon, according to an embodiment of the present disclosure;

FIG. 1E shows a guide catheter with wire and impedance electrodes, according to an embodiment of the present disclosure;

FIG. 1F shows a catheter with multiple detection electrodes, according to an embodiment of the present disclosure;

FIG. 12 shows a side view of a device for sizing a luminal organ or sizing an opening or aperture of a luminal organ, according to the present disclosure;

FIG. 13 shows a device for sizing a luminal organ or sizing an opening or aperture of a luminal organ whereby the balloon is positioned within the opening or aperture, according to the present disclosure;

DETAILED DESCRIPTION

Figure 2B:
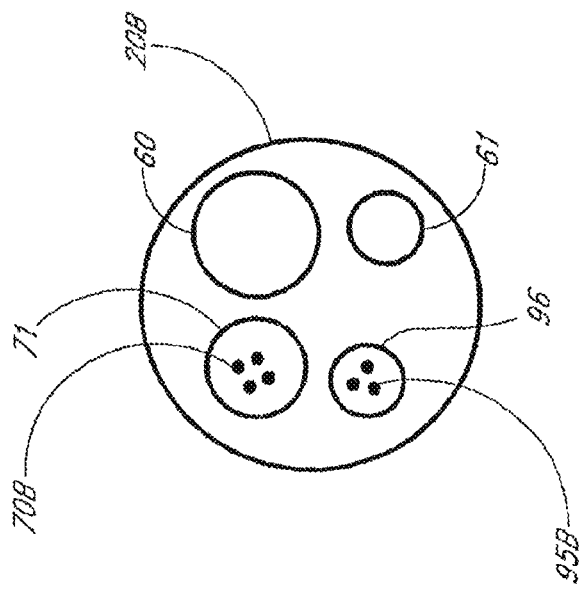
FIG. 2B shows a catheter in cross-section proximal to the location of the sensors showing the leads run in separate lumens, according to an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

This present disclosure makes accurate measures of the luminal cross-sectional area of organ stenosis within acceptable limits to enable accurate and scientific stent sizing and placement in order to improve clinical outcomes by avoiding under or over deployment and under or over sizing of a stent which can cause acute closure or in-stent re-stenosis. In one embodiment, an angioplasty or stent balloon includes impedance electrodes supported by the catheter in front of the balloon. These electrodes enable the immediate measurement of the cross-sectional area of the vessel during the balloon advancement. This provides a direct measurement of non-stenosed area and allows the selection of the appropriate stent size. In one approach, error due to the loss of current in the wall of the organ and surrounding tissue is corrected by injection of two solutions of NaCl or other solutions with known conductivities. In another embodiment impedance electrodes are located in the center of the balloon in order to deploy the stent to the desired cross-sectional area. These embodiments and procedures substantially improve the accuracy of stenting and the outcome and reduce the cost.

Other embodiments make diagnosis of valve stenosis more accurate and more scientific by providing a direct accurate measurement of cross-sectional area of the valve annulus, independent of the flow conditions through the valve. Other embodiments improve evaluation of cross-sectional area and flow in organs like the gastrointestinal tract and the urinary tract.

Embodiments of the present disclosure overcome the problems associated with determination of the size (cross-sectional area) of luminal organs, such as, for example, in the coronary arteries, carotid, femoral, renal and iliac arteries, aorta, gastrointestinal tract, urethra and ureter, Embodiments also provide methods for registration of acute changes in wall conductance, such as, for example, due to edema or acute damage to the tissue, and for detection of muscle spasms/contractions.

As described below, in one preferred embodiment, there is provided an angioplasty catheter with impedance electrodes near the distal end 19 of the catheter (i.e., in front of the balloon) for immediate measurement of the cross-sectional area of a vessel lumen during balloon advancement. This catheter includes electrodes for accurate detection of organ luminal cross-sectional area and ports for pressure gradient measurements. Hence, it is not necessary to change catheters such as with the current use of intravascular ultrasound. In one preferred embodiment, the catheter provides direct measurement of the non-stenosed area, thereby allowing the selection of an appropriately sized stent. In another embodiment, additional impedance electrodes may be incorporated in the center of the balloon on the catheter in order to deploy the stent to the desired cross-sectional area. The procedures described herein substantially improve the accuracy of stenting and improve the cost and outcome as well.

In another embodiment, the impedance electrodes are embedded within a catheter to measure the valve area directly and independent of cardiac output or pressure drop and therefore minimize errors in the measurement of valve area. Hence, measurements of area are direct and not based on calculations with underlying assumptions. In another embodiment, pressure sensors can be mounted proximal and distal to the impedance electrodes to provide simultaneous pressure gradient recording.

Catheter

We designed and build the impedance or conductance catheters illustrated in FIGS. 1A-1F. With reference to the exemplary embodiment shown in FIG. 1A, four wires were threaded through one of the 2 lumens of a 4 Fr catheter. Here, electrodes 26 and 28, are spaced 1 mm apart and form the inner (detection) electrodes. Electrodes 25 and 27 are spaced 4-5 mm from either side of the inner electrodes and form the outer (excitation) electrodes.

In one approach, dimensions of a catheter to be used for any given application depend on the optimization of the potential field using finite element analysis described below. For small organs or in pediatric patients the diameter of the catheter may be as small as 0.3 mm. In large organs the diameter may be significantly larger depending on the results of the optimization based on finite element analysis. The balloon size will typically be sized according to the preferred dimension of the organ after the distension. The balloon may be made of materials, such as, for example, polyethylene, latex, polyestherurethane, or combinations thereof. The thickness of the balloon will typically be on the order of a few microns. The catheter will typically be made of PVC or polyethylene, though other materials may equally well be used. The excitation and detection electrodes typically surround the catheter as ring electrodes but they may also be point electrodes or have other suitable configurations. These electrodes may be made of any conductive material, preferably of platinum iridium or a carbon-coasted surface to avoid fibrin deposits. In the preferred embodiment, the detection electrodes are spaced with 0.5-1 mm between them and with a distance between 4-7 mm to the excitation electrodes on small catheters. The dimensions of the catheter selected for a treatment depend on the size of the vessel and are preferably determined in part on the results of finite element analysis, described below. On large catheters, for use in larger vessels and other visceral hollow organs, the electrode distances may be larger.

Referring to FIGS. 1A, 1B, 1C and 1D, several embodiments of the catheters are illustrated. The catheters shown contain to a varying degree different electrodes, number and optional balloon(s). With reference to the embodiment shown in FIG. 1A, there is shown an impedance catheter 20 with 4 electrodes 25, 26, 27 and 28 placed close to the tip 19 of the catheter. Proximal to these electrodes is an angiography or stenting balloon 30 capable of being used for treating stenosis. Electrodes 25 and 27 are excitation electrodes, while electrodes 26 and 28 are detection electrodes, which allow measurement of cross-sectional area during advancement of the catheter, as described in further detail below. The portion of the catheter 20 within balloon 30 includes an infusion port 35 and a pressure port 36.

The catheter 20 may also advantageously include several miniature pressure transducers (not shown) carried by the catheter or pressure ports for determining the pressure gradient proximal at the site where the cross-sectional area is measured. The pressure is preferably measured inside the balloon and proximal, distal to and at the location of the cross-sectional area measurement, and locations proximal and distal thereto, thereby enabling the measurement of pressure recordings at the site of stenosis and also the measurement of pressure-difference along or near the stenosis. In one embodiment, shown in FIG. 1A, Catheter 20 advantageously includes pressure port 90 and pressure port 91 proximal to or at the site of the cross-sectional measurement for evaluation of pressure gradients. As described below with reference to FIGS. 2A, 2B and 3, in one embodiment, the pressure ports are connected by respective conduits in the catheter 20 to pressure sensors in the data acquisition system 100. Such pressure sensors are well known in the art and include, for example, fiber-optic systems, miniature strain gauges, and perfused low-compliance manometry.

In one embodiment, a fluid-filled silastic pressure-monitoring catheter is connected to a pressure transducer. Luminal pressure can be monitored by a low compliance external pressure transducer coupled to the infusion channel of the catheter. Pressure transducer calibration was carried out by applying 0 and 100 mmHg of pressure by means of a hydrostatic column.

In one embodiment, shown in FIG. 1B, the catheter 39 includes another set of excitation electrodes 40, 41 and detection electrodes 42, 43 located inside the angioplastic or stenting balloon 30 for accurate determination of the balloon cross-sectional area during angioplasty or stent deployment. These electrodes are in addition to electrodes 25, 26, 27 and 28.

In one embodiment, the cross-sectional area may be measured using a two-electrode system. In another embodiment, illustrated in FIG. 1F, several cross-sectional areas can be measured using an array of 5 or more electrodes. Here, the excitation electrodes 51, 52, are used to generate the current while detection electrodes 53, 54, 55, 56 and 57 are used to detect the current at their respective sites.

The tip of the catheter can be straight, curved or with an angle to facilitate insertion into the coronary arteries or other lumens, such as, for example, the biliary tract. The distance between the balloon and the electrodes is usually small, in the 0.5-2 cm range but can be closer or further away, depending on the particular application or treatment involved.

In another embodiment, shown in FIG. 1C the catheter 21 has one or more imaging or recording device, such as, for example, ultrasound transducers 50 for cross-sectional area and wall thickness measurements. As shown in this embodiment, the transducers 50 are located near the distal tip 19 of the catheter 21.

FIG. 1D shows an embodiment of the impedance catheter 22 without an angioplastic or stenting balloon. This catheter also possesses an infusion or injection port 35 located proximal relative to the excitation electrode 25 and pressure port 36.

With reference to the embodiment shown in FIG. 1E, the electrodes 25, 26, 27, 28 can also be built onto a wire 18, such as, for example, a pressure wire, and inserted through a guide catheter 23 where the infusion of bolus can be made through the lumen of the guide catheter 37.

With reference to the embodiments shown in FIGS. 1A, 1B, 1C, 1D, 1E and 1F, the impedance catheter advantageously includes optional ports 35, 36, 37 for suction of contents of the organ or infusion of fluid. The suction/infusion port 35, 36, 37 can be placed as shown with the balloon or elsewhere both proximal or distal to the balloon on the catheter. The fluid inside the balloon can be any biologically compatible conducting fluid. The fluid to inject through the infusion port or ports can be any biologically compatible fluid but the conductivity of the fluid is selected to be different from that of blood (e.g., NaCl).

In another embodiment (not illustrated), the catheter contains an extra channel for insertion of a guide wire to stiffen the flexible catheter during the insertion or data recording. In yet another embodiment (not illustrated), the catheter includes a sensor for measurement of the flow of fluid in the body organ.

System for Determining Cross-Sectional Area and Pressure Gradient

The operation of the impedance catheter 20 is as follows: With reference to the embodiment shown in FIG. 1A for electrodes 25, 26, 27, 28, conductance of current flow through the organ lumen and organ wall and surrounding tissue is parallel; i.e., $$G(z, t) = \frac{CSA(z, t) \cdot C_b}{L} + G_p(z, t) \quad [1a]$$

where $G_p(z,t)$ is the effective conductance of the structure outside the bodily fluid (organ wall and surrounding tissue), and $C_b$ is the specific electrical conductivity of the bodily fluid which for blood generally depends on the temperature, hematocrit and orientation and deformation of blood cells and L is the distance between the detection electrodes. Equation [1] can be rearranged to solve for cross sectional area CSA(t), with a correction factor, $\alpha$, if the electric field is non-homogeneous, as $$CSA(z, t) = \frac{L}{\alpha C_b}[G(z, t) - G_p(z, t)] \quad [1b]$$

where $\alpha$ would be equal to 1 if the field were completely homogeneous. The parallel conductance, $G_p$, is an offset error that results from current leakage. $G_p$ would equal 0 if all of the current were confined to the blood and hence would correspond to the cylindrical model given by Equation [10]. In one approach, finite element analysis is used to properly design the spacing between detection and excitation electrodes relative to the dimensions of the vessel to provide a nearly homogenous field such that a can be considered equal to 1. Our simulations show that a homogenous or substantially homogenous field is provided by (1) the placement of detection electrodes substantially equidistant from the excitation electrodes and (2) maintaining the distance between the detection and excitation electrodes substantially comparable to the vessel diameter. In one approach, a homogeneous field is achieved by taking steps (1) and/or (2) described above so that $\alpha$ is equals 1 in the foregoing analysis.

At any given position, z, along the long axis of organ and at any given time, t, in the cardiac cycle, $G_p$ is a constant. Hence, two injections of different concentrations and/or conductivities of NaCl solution give rise to two Equations:

$$C_1 \cdot CSA(z,t) + L \cdot G_p(z,t) = L \cdot G_1(z,t) \quad [2]$$

and $$C_2 \cdot CSA(z,t) + L \cdot G_p(z,t) = L \cdot G_2(z,t) \quad [3]$$

which can be solved simultaneously for CSA and $G_p$ as $$CSA(z, t) = L\frac{[G_2(z, t) - G_1(z, t)]}{[C_2 - C_1]} \quad [4]$$

and $$G_p(z, t) = \frac{[C_2 \cdot G_1(z, t) - C_1 \cdot G_2(z, t)]}{[C_2 - C_1]} \quad [5]$$

where subscript "1" and subscript "2" designate any two injections of different NaCl concentrations and/or conductivities. For each injection k, $C_k$ gives rise to $G_k$ which is measured as the ratio of the root mean square of the current divided by the root mean square of the voltage. The $C_k$ is typically determined through in vitro calibration for the various NaCl concentrations and/or conductivities. The concentration of NaCl used is typically on the order of 0.45 to 1.8%. The volume of NaCl solution is typically about 5 ml, but sufficient to displace the entire local vascular blood volume momentarily. The values of CSA(t) and $G_p$(t) can be determined at end-diastole or end-systole (i.e., the minimum and maximum values) or the mean thereof.

Once the CSA and $G_p$ of the vessel are determined according to the above embodiment, rearrangement of Equation [1] allows the calculation of the specific electrical conductivity of blood in the presence of blood flow as $$C_b = \frac{L}{CSA(z, t)}[G(z, t) - G_p(z, t)] \quad [6]$$

In this way, Equation [1b] can be used to calculate the CSA continuously (temporal variation as for example through the cardiac cycle) in the presence of blood.

In one approach, a pull or push through is used to reconstruct the vessel along its length. During a long injection (e.g., 10-15 s), the catheter can be pulled back or pushed forward at constant velocity U. Equation [1b] can be expressed as $$CSA(U \cdot t, t) = \frac{L}{C_b}[G(U \cdot t, t) - G_p(U \cdot (t, t)] \quad [7]$$

where the axial position, z, is the product of catheter velocity, U, and time, t; i.e., z=U•t.

For the two injections, denoted by subscript "1" and subscript "2", respectively, we can consider different time points T1, T2, etc. such that Equation [7] can be written as $$CSA_1(U \cdot T_1, t) = \frac{L}{C_1}[G_1(U \cdot T_1, t) - G_{p1}(U \cdot (T_1, t)] \quad [8a]$$

$$CSA_1(U \cdot T_1, t) = \frac{L}{C_2}[G_2(U \cdot T_1, t) - G_{p1}(U \cdot (T_1, t)] \quad [8b]$$

and $$CSA_2(U \cdot T_2, t) = \frac{L}{C_1}[G_1(U \cdot T_2, t) - G_{p2}(U \cdot (T_2, t)] \quad [9a]$$

-continued $$CSA_2(U \cdot T_2, t) = \frac{L}{C_2}[G_2(U \cdot T_2, t) - G_{p2}(U \cdot (T_2, t)]$$ [9b]

and so on. Each set of Equations [8a], [8b] and [9a], [9b], etc. can be solved for $GSA_1$, $G_{p1}$ and $CSA_2$, $G_{p2}$, respectively. Hence, we can measure the CSA at various time intervals and hence of different positions along the vessel to reconstruct the length of the vessel. In one embodiment, the data on the CSA and parallel conductance as a function of longitudinal position along the vessel can be exported from an electronic spreadsheet, such as, for example, an Excel file, to AutoCAD where the software uses the coordinates to render a 3-Dimensional vessel on the monitor.

For example, in one exemplary approach, the pull back reconstruction was made during a long injection where the catheter was pulled back at constant rate by hand. The catheter was marked along its length such that the pull back was made at 2 mm/sec. Hence, during a 10 second injection, the catheter was pulled back about 2 cm. The data was continuously measured and analyzed at every two second interval; i.e., at every 4 mm. Hence, six different measurements of CSA and $G_p$ were made which were used to reconstruction the CSA and $G_p$ along the length of the 2 cm segment.

Operation of the impedance catheter 39: With reference to the embodiment shown in FIG. 1B, the voltage difference between the detection electrodes 42 and 43 depends on the magnitude of the current (I) multiplied by the distance (D) between the detection electrodes and divided by the conductivity (C) of the fluid and the cross-sectional area (CSA) of the artery or other organs into which the catheter is introduced. Since the current (I), the distance (L) and the conductivity (C) normally can be regarded as calibration constants, an inverse relationship exists between the voltage difference and the CSA as shown by the following Equations:

$$\Delta V = \frac{I \cdot L}{C \cdot CSA}$$ [10a]

or $$CSA = \frac{G \cdot L}{C}$$ [10b]

where G is conductance expressed as the ratio of current to voltage (I/$\Delta$V). Equation [10] is identical to Equation [1b] if we neglect the parallel conductance through the vessel wall and surrounding tissue because the balloon material acts as an insulator. This is the cylindrical model on which the conductance method is used.

As described below with reference to FIGS. 2A, 2B, 3, 4 and 5, the excitation and detection electrodes are electrically connected to electrically conductive leads in the catheter for connecting the electrodes to the data acquisition system 100.

Figure 2A:
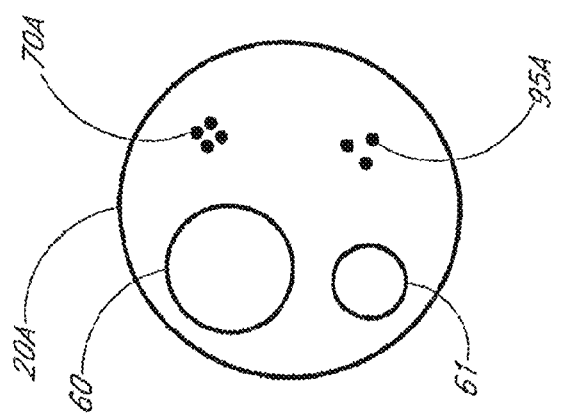
FIG. 2A shows a catheter in cross-section proximal to the location of the sensors showing the leads embedded in the material of the probe, according to an embodiment of the present disclosure.

FIGS. 2A and 2B illustrate two embodiments 20A and 20B of the catheter in cross-section. Each embodiment has a lumen 60 for inflating and deflating the balloon and a lumen 61 for suction and infusion. The sizes of these lumens can vary in size. The impedance electrode electrical leads 70A are embedded in the material of the catheter in the embodiment in FIG. 2A, whereas the electrode electrical leads 70B are tunneled through a lumen 71 formed within the body of catheter 70B in FIG. 2B.

Pressure conduits for perfusion manometry connect the pressure ports 90, 91 to transducers included in the data acquisition system 100. As shown in FIG. 2A pressure conduits 95A may be formed in 20A. In another embodiment, shown in FIG. 2B, pressure conduits 95B constitute individual conduits within a tunnel 96 formed in catheter 20B. In the embodiment described above where miniature pressure transducers are carried by the catheter, electrical conductors will be substituted for these pressure conduits.

Figure 3:
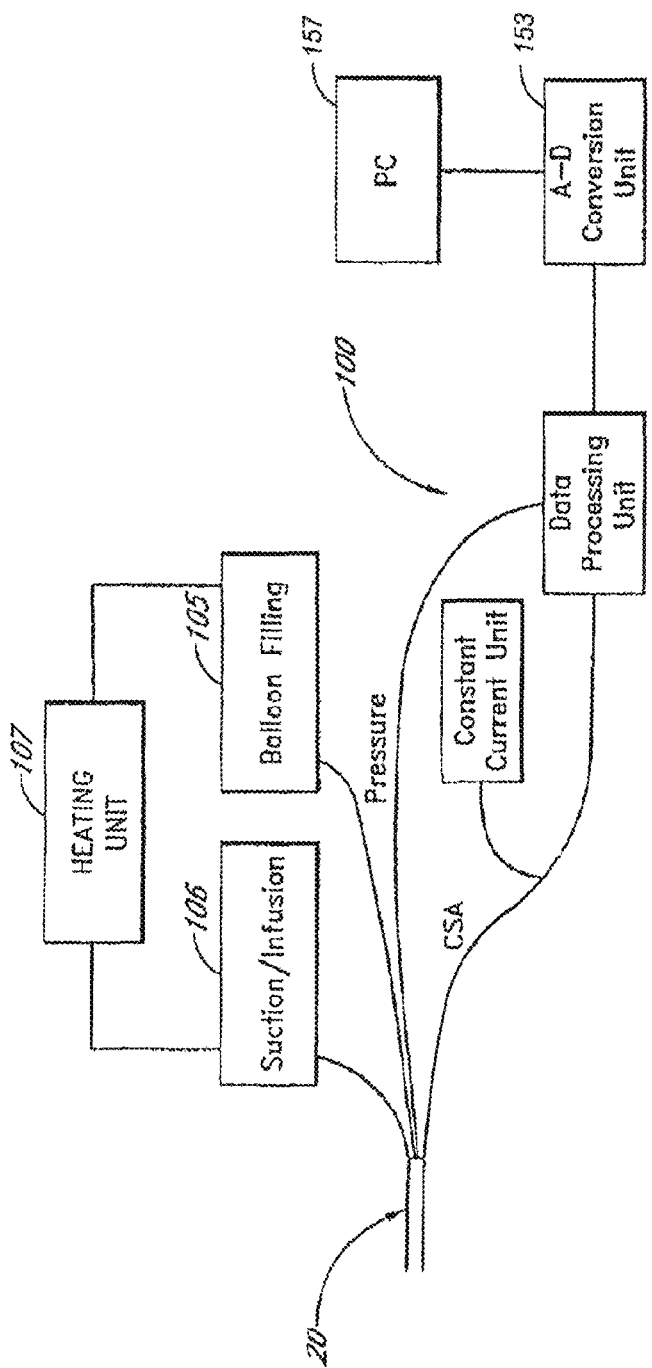
FIG. 3 is a schematic of one embodiment of the system showing a catheter carrying impedance measuring electrodes connected to the data acquisition equipment and excitation unit for the cross-sectional area measurement, according to an embodiment of the present disclosure.

With reference to FIG. 3, in one embodiment, the catheter 20 connects to a data acquisition system 100, to a manual or automatic system 105 for distension of the balloon and to a system 106 for infusion of fluid or suction of blood. The fluid will be heated to 37-39° or equivalent to body temperature with heating unit 107. The impedance planimetry system typically includes a current unit, amplifiers and signal conditioners. The pressure system typically includes amplifiers and signal conditioners. The system can optionally contain signal conditioning equipment for recording of fluid flow in the organ.

In one preferred embodiment, the system is pre-calibrated and the probe is available in a package. Here, the package also preferably contains sterile syringes with the fluids to be injected. The syringes are attached to the machine and after heating of the fluid by the machine and placement of the probe in the organ of interest, the user presses a button that initiates the injection with subsequent computation of the desired parameters. The CSA and parallel conductance and other relevant measures such as distensibility, tension, etc. will typically appear on the display panel in the PC module 160. Here, the user can then remove the stenosis by distension or by placement of a stent.

If more than one CSA is measured, the system can contain a multiplexer unit or a switch between CSA channels. In one embodiment, each CSA measurement will be through separate amplifier units. The same may account for the pressure channels.

In one embodiment, the impedance and pressure data are analog signals which are converted by analog-to-digital converters 153 and transmitted to a computer 157 for on-line display, on-line analysis and storage. In another embodiment, all data handling is done on an entirely analog basis. The analysis advantageously includes software programs for reducing the error due to conductance of current in the organ wall and surrounding tissue and for displaying the 2D or 3D-geometry of the CSA distribution along the length of the vessel along with the pressure gradient. In one embodiment of the software, a finite element approach or a finite difference approach is used to derive the CSA of the organ stenosis taking parameters such as conductivities of the fluid in the organ and of the organ wall and surrounding tissue into consideration. In another embodiment, simpler circuits are used; e.g., based on making two or more injections of different NaCl solutions to vary the resistivity of fluid in the vessel and solving the two simultaneous Equations [2] and [3] for the CSA and parallel conductance (Equations [4] and [5], respectively). In another embodiment, the software contains the code for reducing the error in luminal CSA measurement by analyzing signals during interventions such as infusion of a fluid into the organ or by changing the amplitude or frequency of the current from the current amplifier, which may be a constant current amplifier. The software chosen for a particular application, preferably allows computation of the CSA with only a small error instantly or within acceptable time during the medical procedure.

In one approach, the wall thickness is determined from the parallel conductance for those organs that are surrounded by air or non-conducting tissue. In such cases, the parallel conductance is equal to $$G_p = \frac{CSA_w \cdot C_w}{L} \quad [11a]$$

where $CSA_W$ is the wall area of the organ and $C_W$ is the electrical conductivity through the wall.

This Equation can be solved for the wall $CSA_W$ as $$CSA_w = \frac{G_p \cdot L}{C_w} \quad [11b]$$

For a cylindrical organ, the wall thickness, h, can be expressed as $$h = \frac{CSA_w}{\pi D} \quad [12]$$

where D is the diameter of the vessel which can be determined from the circular CSA ($D=[4CSA/\pi]^{1/2}$).

When the CSA, pressure, wall thickness, and flow data are determined according to the embodiments outlined above, it is possible to compute the compliance (e.g., $\Delta CSA/\Delta P$), tension (e.g., P·r, where P and r are the intraluminal pressure and radius of a cylindrical organ), stress (e.g., P·r/h where h is the wall thickness of the cylindrical organ), strain (e.g., $(C-C_d)/C_d$ where C is the inner circumference and $C_d$ is the circumference in diastole) and wall shear stress (e.g., $4 \mu Q/r^3$ where μ, Q and r are the fluid viscosity, flow rate and radius of the cylindrical organ for a fully developed flow). These quantities can be used in assessing the mechanical characteristics of the system in health and disease.

Method

In one approach, luminal cross-sectional area is measured by introducing a catheter from an exteriorly accessible opening (e.g., mouth, nose or anus for GI applications; or e.g., mouth or nose for airway applications) into the hollow system or targeted luminal organ. For cardiovascular applications, the catheter can be inserted into the organs in various ways; e.g., similar to conventional angioplasty. In one embodiment, an 18 gauge needle is inserted into the femoral artery followed by an introducer. A guide wire is then inserted into the introducer and advanced into the lumen of the femoral artery. A 4 or 5 Fr conductance catheter is then inserted into the femoral artery via wire and the wire is subsequently retracted. The catheter tip containing the conductance electrodes can then be advanced to the region of interest by use of x-ray (i.e., fluoroscopy). In another approach, this methodology is used on small to medium size vessels (e.g., femoral, coronary, carotid, iliac arteries, etc.).

In one approach, a minimum of two injections (with different concentrations and/or conductivities of NaCl) are required to solve for the two unknowns, CSA and $G_p$. In another approach, three injections will yield three set of values for CSA and $G_p$ (although not necessarily linearly independent), while four injections would yield six set of values. In one approach, at least two solutions (e.g., 0.5% and 1.5% NaCl solutions) are injected in the targeted luminal organ or vessel. Our studies indicate that an infusion rate of approximately 1 ml/s for a five second interval is sufficient to displace the blood volume and results in a local pressure increase of less than 10 mmHg in the coronary artery. This pressure change depends on the injection rate which should be comparable to the organ flow rate.

In one preferred approach, involving the application of Equations [4] and [5], the vessel is under identical or very similar conditions during the two injections. Hence, variables, such as, for example, the infusion rate, bolus temperature, etc., are similar for the two injections. Typically, a short time interval is to be allowed (1-2 minute period) between the two injections to permit the vessel to return to homeostatic state. This can be determined from the baseline conductance as shown in FIG. 4 or 5. The parallel conductance is preferably the same or very similar during the two injections. In one approach, dextran, albumin or another large molecular weight molecule can be added to the NaCl solutions to maintain the colloid osmotic pressure of the solution to reduce or prevent fluid or ion exchange through the vessel wall.

In one approach, the NaCl solution is heated to body temperature prior to injection since the conductivity of current is temperature dependent. In another approach, the injected bolus is at room temperature, but a temperature correction is made since the conductivity is related to temperature in a linear fashion.

In one approach, a sheath is inserted either through the femoral or carotid artery in the direction of flow. To access the lower anterior descending (LAD) artery, the sheath is inserted through the ascending aorta. For the carotid artery, where the diameter is typically on the order of 5-5.5 mm, a catheter having a diameter of 1.9 mm can be used, as determined from finite element analysis, discussed further below. For the femoral and coronary arteries, where the diameter is typically in the range from 3.5-4 mm, so a catheter of about 0.8 mm diameter would be appropriate. The catheter can be inserted into the femoral, carotid or LAD artery through a sheath appropriate for the particular treatment. Measurements for all three vessels can be made similarly.

Described here are the protocol and results for one exemplary approach that is generally applicable to most arterial vessels. The conductance catheter was inserted through the sheath for a particular vessel of interest. A baseline reading of voltage was continuously recorded. Two containers containing 0.5% and 1.5% NaCl were placed in temperature bath and maintained at 37°. A 5-10 ml injection of 1.5% NaCl was made over a 5 second interval. The detection voltage was continuously recorded over a 10 second interval during the 5 second injection. Several minutes later, a similar volume of 1.5% NaCl solution was injected at a similar rate. The data was again recorded. Matlab was used to analyze the data including filtering with high pass and with low cut off frequency (1200 Hz). The data was displayed using Matlab and the mean of the voltage signal during the passage of each respective solution was recorded. The corresponding currents were also measured to yield the conductance (G=I/V). The conductivity of each solution was calibrated with six different tubes of known CSA at body temperature. A model using Equation [10] was fitted to the data to calculate conductivity C. The analysis was carried out in SPSS using the non-linear regression fit. Given C and G for each of the two injections, an excel sheet file was formatted to calculate the CSA and $G_p$ as per Equations [4] and [5], respectively. These measurements were repeated several times to determine the reproducibility of the technique. The reproducibility of the data was within 5%. Ultrasound (US) was used to measure the diameter of the vessel simultaneous with our conductance measurements. The detection electrodes were visualized with US and the diameter measurements was made at the center of the detection electrodes. The maximum differences between the conductance and US measurements were within 10%.

FIGS. 4A, 4B, 5A and 5B illustrate voltage measurements in the blood stream in the left carotid artery. Here, the data acquisition had a sampling frequency of 75 KHz, with two channels—the current injected and the detected voltage, respectively. The current injected has a frequency of 5 KH, so the voltage detected, modulated in amplitude by the impedance changing through the bolus injection will have a spectrum in the vicinity of 5 KHz.

Figure 4A:
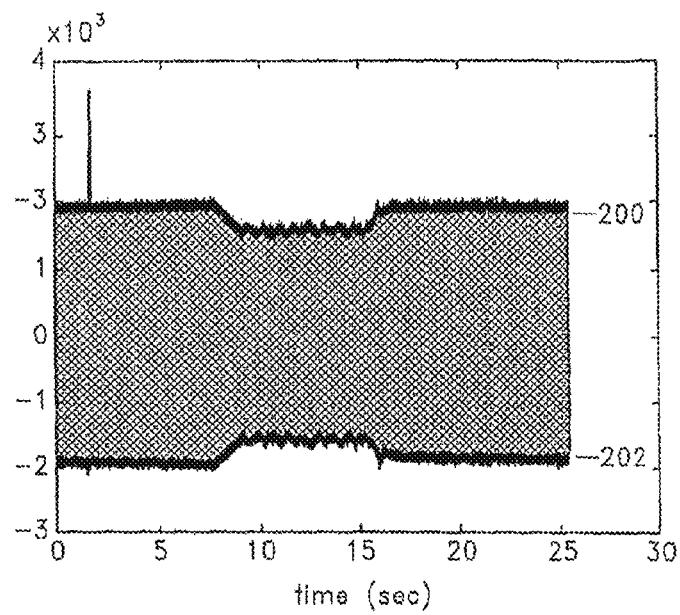
FIG. 4A shows the detected filtered voltage drop as measured in the blood stream before and after injection of 1.5% NaCl solution, according to an embodiment of the present disclosure.
Figure 4B:
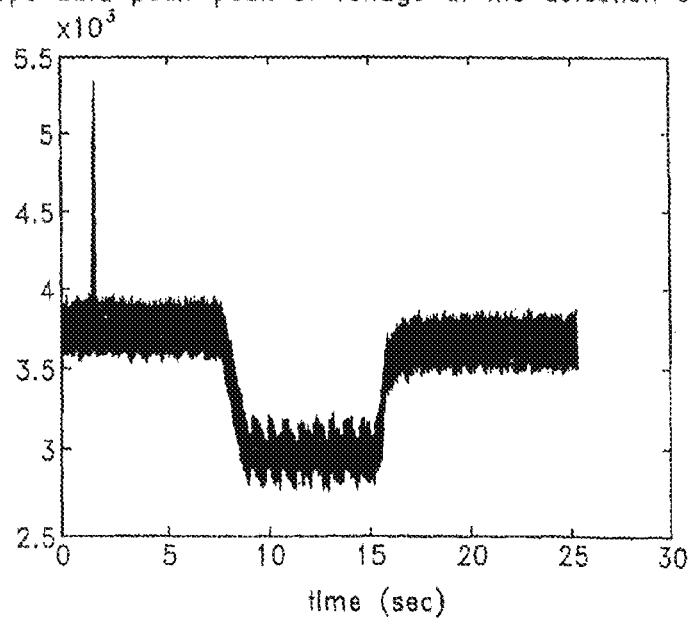
FIG. 4B shows the peak-to-peak envelope of the detected voltage shown in FIG. 4A, according to an embodiment of the present disclosure.
Figure 5A:
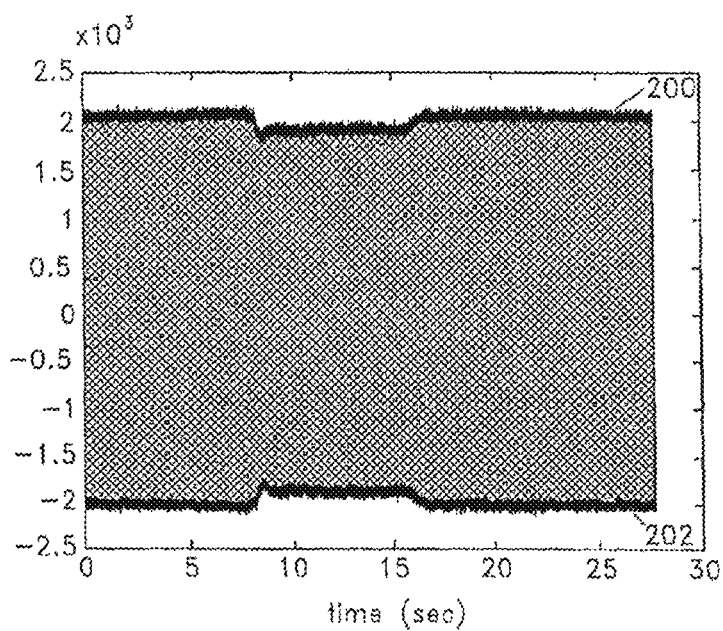
FIG. 5A shows the detected filtered voltage drop as measured in the blood stream before and after injection of 0.5% NaCl solution, according to an embodiment of the present disclosure.
Figure 5B:
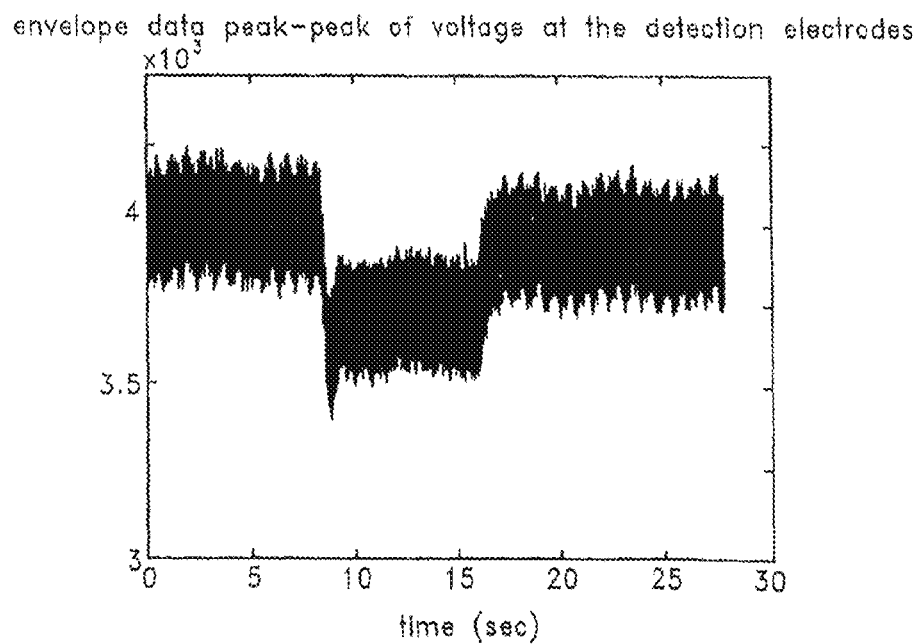
FIG. 5B shows the peak-to-peak envelope of the detected voltage shown in FIG. 5A, according to an embodiment of the present disclosure.

With reference to FIG. 4A there is shown a signal processed with a high pass filter with low cut off frequency (1200 Hz). The top and bottom portions 200, 202 show the peak-to-peak envelope detected voltage which is displayed in FIG. 4B (bottom). The initial 7 seconds correspond to the baseline; i.e., electrodes in the blood stream. The next 7 seconds correspond to an injection of hyper-osmotic NaCl solution (1.5% NaCl). It can be seen that the voltage is decreased implying increase conductance (since the injected current is constant). Once the NaCl solution is washed out, the baseline is recovered as can be seen in the last portion of the FIGS. 4A and 4B. FIGS. 5A and 5B show similar data corresponding to 0.5% NaCl solutions.

The voltage signals are ideal since the difference between the baseline and the injected solution is apparent and systematic. Furthermore, the pulsation of vessel diameter can be seen in the 0.5% and 1.5% NaCl injections (FIGS. 4 and 5, respectively). This allows determination of the variation of CSA throughout the cardiac cycle as outline above.

The NaCl solution can be injected by hand or by using a mechanical injector to momentarily displace the entire volume of blood or bodily fluid in the vessel segment of interest. The pressure generated by the injection will not only displace the blood in the antegrade direction (in the direction of blood flow) but also in the retrograde direction (momentarily push the blood backwards). In other visceral organs which may be normally collapsed, the NaCl solution will not displace blood as in the vessels but will merely open the organs and create a flow of the fluid. In one approach, after injection of a first solution into the treatment or measurement site, sensors monitor and confirm baseline of conductance prior to injection of a second solution into the treatment site.

The injections described above are preferably repeated at least once to reduce errors associated with the administration of the injections, such as, for example, where the injection does not completely displace the blood or where there is significant mixing with blood. It will be understood that any bifurcation(s) (with branching angle near 90 degrees) near the targeted luminal organ can cause an overestimation of the calculated CSA. Hence, generally the catheter should be slightly retracted or advanced and the measurement repeated. An additional application with multiple detection electrodes or a pull back or push forward during injection will accomplish the same goal. Here, an array of detection electrodes can be used to minimize or eliminate errors that would result from bifurcations or branching in the measurement or treatment site.

In one approach, error due to the eccentric position of the electrode or other imaging device can be reduced by inflation of a balloon on the catheter. The inflation of balloon during measurement will place the electrodes or other imaging device in the center of the vessel away from the wall. In the case of impedance electrodes, the inflation of balloon can be synchronized with the injection of bolus where the balloon inflation would immediately precede the bolus injection. Our results, however, show that the error due to catheter eccentricity is small.

The CSA predicted by Equation [4] corresponds to the area of the vessel or organ external to the catheter (i.e., CSA of vessel minus CSA of catheter). If the conductivity of the NaCl solutions is determined by calibration from Equation [10] with various tubes of known CSA, then the calibration accounts for the dimension of the catheter and the calculated CSA corresponds to that of the total vessel lumen as desired. In one embodiment, the calibration of the CSA measurement system will be performed at 37° C. by applying 100 mmHg in a solid polyphenolenoxide block with holes of known CSA ranging from 7.065 $mm^2$ (3 mm in diameter) to 1017 $mm^2$ (36 in mm). If the conductivity of the solutions is obtained from a conductivity meter independent of the catheter, however, then the CSA of the catheter is generally added to the CSA computed from Equation [4] to give the desired total CSA of the vessel.

The signals are generally non-stationary, nonlinear and stochastic. To deal with non-stationary stochastic functions, one can use a number of methods, such as the Spectrogram, the Wavelet's analysis, the Wigner-Ville distribution, the Evolutionary Spectrum, Modal analysis, or preferably the intrinsic model function (IMF) method. The mean or peak-to-peak values can be systematically determined by the aforementioned signal analysis and used in Equation [4] to compute the CSA.

Figure 6:
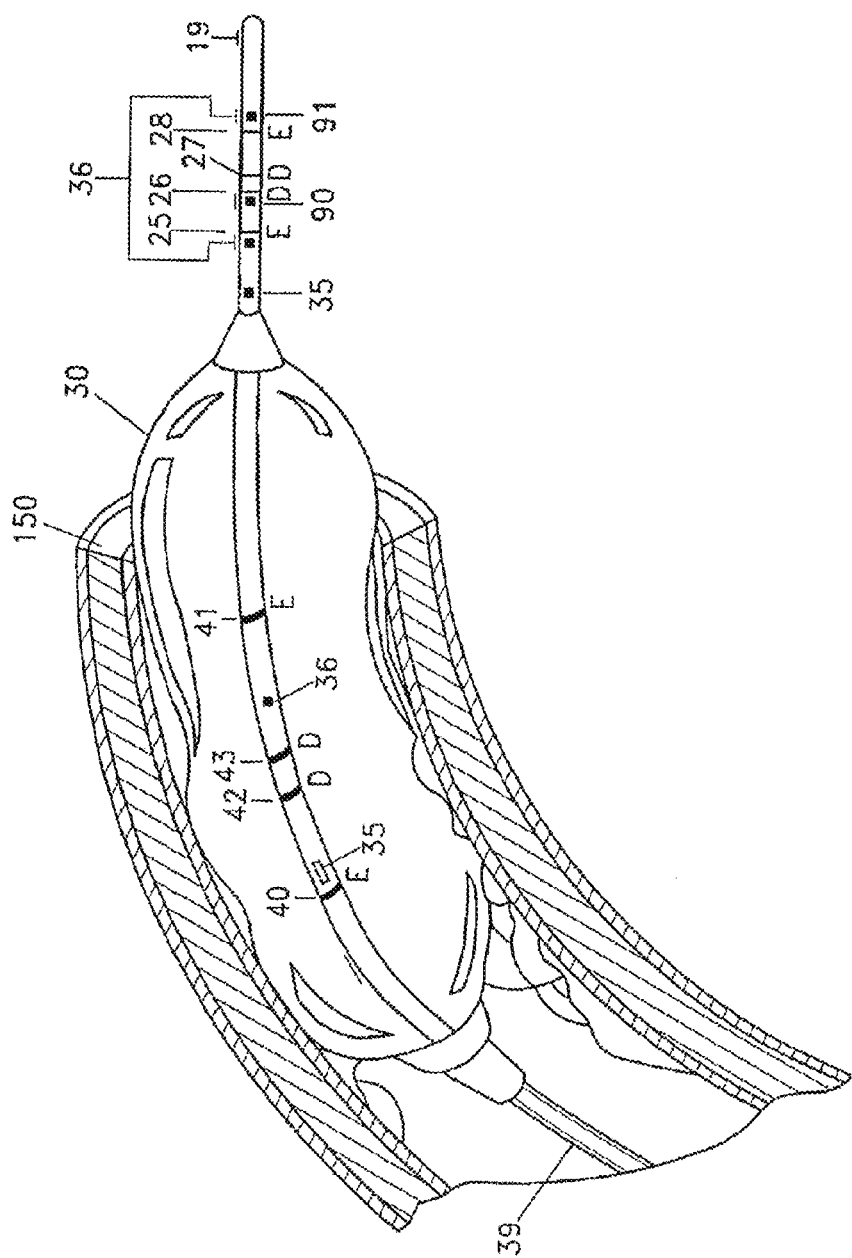
FIG. 6 shows balloon distension of the lumen of the coronary artery, according to an embodiment of the present disclosure.
Figure 7A:
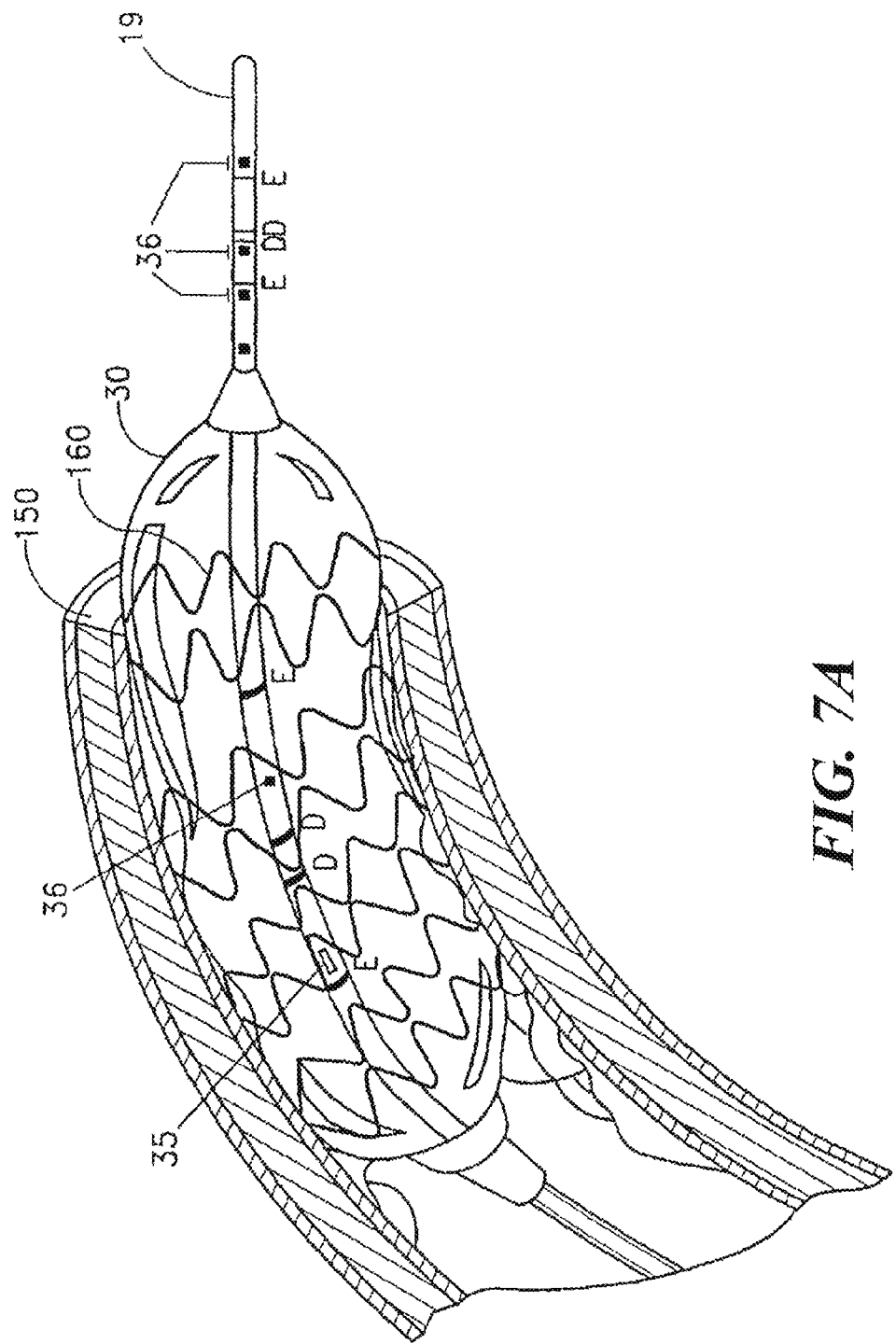
FIG. 7A shows balloon distension of a stent into the lumen of the coronary artery, according to an embodiment of the present disclosure.

Referring to the embodiment shown in FIG. 6, the angioplasty balloon 30 is shown distended within the coronary artery 150 for the treatment of stenosis. As described above with reference to FIG. 1B, a set of excitation electrodes 40, 41 and detection electrodes 42, 43 are located within the angioplasty balloon 30. In another embodiment, shown in FIG. 7A, the angioplasty balloon 30 is used to distend the stent 160 within blood vessel 150.

For valve area determination, it is not generally feasible to displace the entire volume of the heart. Hence, the conductivity of blood is changed by injection of hypertonic NaCl solution into the pulmonary artery which will transiently change the conductivity of blood. If the measured total conductance is plotted versus blood conductivity on a graph, the extrapolated conductance at zero conductivity corresponds to the parallel conductance. In order to ensure that the two inner electrodes are positioned in the plane of the valve annulus (2-3 mm), in one preferred embodiment, the two pressure sensors 36 are advantageously placed immediately proximal and distal to the detection electrodes (1-2 mm above and below, respectively) or several sets of detection electrodes (see, e.g., FIGS. 1D and 1F). The pressure readings will then indicate the position of the detection electrode relative to the desired site of measurement (aortic valve: aortic-ventricular pressure; mitral valve: left ventricular-atrial pressure; tricuspid valve: right atrial-ventricular pressure; pulmonary valve: right ventricular-pulmonary pressure). The parallel conductance at the site of annulus is generally expected to be small since the annulus consists primarily of collagen which has low electrical conductivity. In another application, a pull back or push forward through the heart chamber will show different conductance due to the change in geometry and parallel conductance. This can be established for normal patients which can then be used to diagnose valvular stenososis.

In one approach, for the esophagus or the urethra, the procedures can conveniently be done by swallowing fluids of known conductances into the esophagus and infusion of fluids of known conductances into the urinary bladder followed by voiding the volume. In another approach, fluids can be swallowed or urine voided followed by measurement of the fluid conductances from samples of the fluid. The latter method can be applied to the ureter where a catheter can be advanced up into the ureter and fluids can either be injected from a proximal port on the probe (will also be applicable in the intestines) or urine production can be increased and samples taken distal in the ureter during passage of the bolus or from the urinary bladder.

In one approach, concomitant with measuring the cross-sectional area and or pressure gradient at the treatment or measurement site, a mechanical stimulus is introduced by way of inflating the balloon or by releasing a stent from the catheter, thereby facilitating flow through the stenosed part of the organ. In another approach, concomitant with measuring the cross-sectional area and or pressure gradient at the treatment site, one or more pharmaceutical substances for diagnosis or treatment of stenosis is injected into the treatment site. For example, in one approach, the injected substance can be smooth muscle agonist or antagonist. In yet another approach, concomitant with measuring the cross-sectional area and or pressure gradient at the treatment site, an inflating fluid is released into the treatment site for release of any stenosis or materials causing stenosis in the organ or treatment site.

Again, it will be noted that the methods, systems, and catheters described herein can be applied to any body lumen or treatment site. For example, the methods, systems, and catheters described herein can be applied to any one of the following exemplary bodily hollow systems: the cardiovascular system including the heart; the digestive system; the respiratory system; the reproductive system; and the urogential tract.

Finite Element Analysis: In one preferred approach, finite element analysis (FEA) is used to verify the validity of Equations [4] and [5]. There are two major considerations for the model definition: geometry and electrical properties. The general Equation governing the electric scalar potential distribution, V, is given by Poisson's Equation as:

$$\nabla \cdot (C \nabla V) = -I \quad [13]$$

where C, I and V are the conductivity, the driving current density and the del operator, respectively. Femlab or any standard finite element packages can be used to compute the nodal voltages using Equation [13]. Once V has been determined, the electric field can be obtained from as $E = -\nabla V$.

The FEA allows the determination of the nature of the field and its alteration in response to different electrode distances, distances between driving electrodes, wall thicknesses and wall conductivities. The percentage of total current in the lumen of the vessel (% I) can be used as an index of both leakage and field homogeneity. Hence, the various geometric and electrical material properties can be varied to obtain the optimum design; i.e., minimize the non-homogeneity of the field. Furthermore, we simulated the experimental procedure by injection of the two solutions of NaCl to verify the accuracy of Equation [4]. Finally, we assessed the effect of presence of electrodes and catheter in the lumen of vessel. The error terms representing the changes in measured conductance due to the attraction of the field to the electrodes and the repulsion of the field from the resistive catheter body were quantified.

We solved the Poisson's Equation for the potential field which takes into account the magnitude of the applied current, the location of the current driving and detection electrodes, and the conductivities and geometrical shapes in the model including the vessel wall and surrounding tissue. This analysis suggest that the following conditions are optimal for the cylindrical model: (1) the placement of detection electrodes equidistant from the excitation electrodes; (2) the distance between the current driving electrodes should be much greater than the distance between the voltage sensing electrodes; and (3) the distance between the detection and excitation electrodes is comparable to the vessel diameter or the diameter of the vessel is small relative to the distance between the driving electrodes. If these conditions are satisfied, the equipotential contours more closely resemble straight lines perpendicular to the axis of the catheter and the voltage drop measured at the wall will be nearly identical to that at the center. Since the curvature of the equipotential contours is inversely related to the homogeneity of the electric field, it is possible to optimize the design to minimize the curvature of the field lines. Consequently, in one preferred approach, one or more of conditions (1)-(3) described above are met to increase the accuracy of the cylindrical model.

Figure 7B:
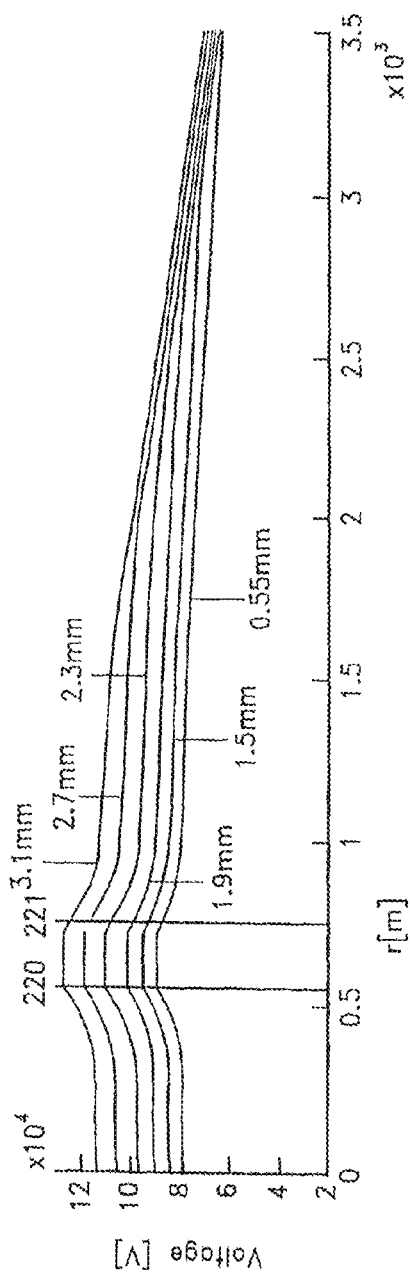
FIG. 7B shows the voltage recorded by a conductance catheter with a radius of 0.55 mm for various size vessels (vessel radii of 3.1, 2.7, 2.3, 1.9, 1.5 and 0.55 mm for the six curves, respectively) when a 0.5% NaCl bolus is injected into the treatment site, according to an embodiment of the present disclosure.
Figure 7C:
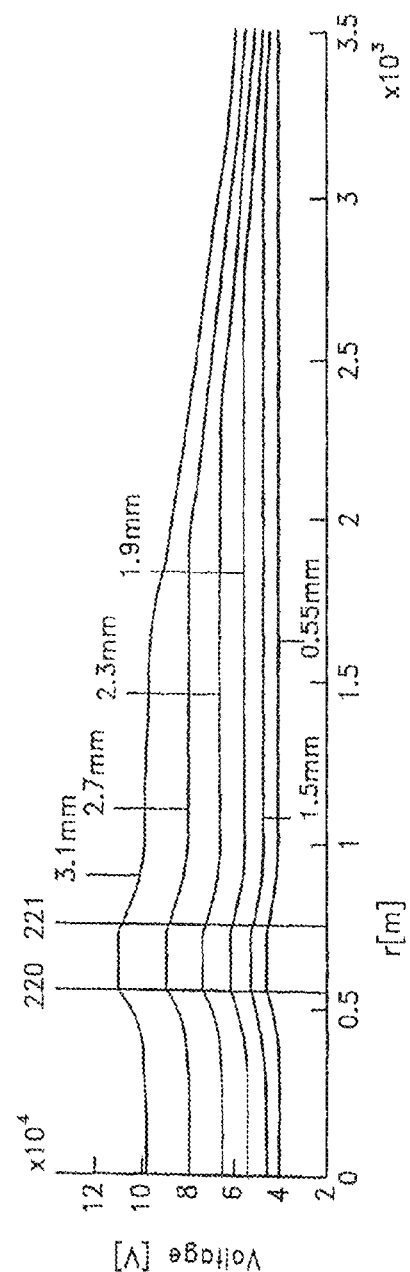
FIG. 7C shows the voltage recorded by a conductance catheter with a radius of 0.55 mm for various size vessels (vessel radii of 3.1, 2.7, 2.3, 1.9, 1.5 and 0.55 mm for the six curves, respectively) when a 1.5% NaCl bolus is injected into the treatment site, according to an embodiment of the present disclosure.

Theoretically, it is impossible to ensure a completely homogeneous field given the current leakage through the vessel wall into the surrounding tissue. We found that the iso-potential line is not constant as we move out radially along the vessel as stipulated by the cylindrical model. In one embodiment, we consider a catheter with a radius of 0.55 mm whose detected voltage is shown in FIGS. 7B and 7C for two different NaCl solutions (0.5% and 1.5%, respectively). The origin corresponds to the center of the catheter. The first vertical line 220 represents the inner part of the electrode which is wrapped around the catheter and the second vertical line 221 is the outer part of the electrode in contact with the solution (diameter of electrode is approximately 0.25 mm). The six different curves, top to bottom, correspond to six different vessels with radii of 3.1, 2.7, 2.3, 1.9, 1.5 and 0.55 mm, respectively. It can be seen that a "hill" occurs at the detection electrode 220, 221 followed by a fairly uniform plateau in the vessel lumen followed by an exponential decay into the surrounding tissue. Since the potential difference is measured at the detection electrode 220, 221, our simulation generates the "hill" whose value corresponds to the equivalent potential in the vessel as used in Equation [4]. Hence, for each catheter size, we varied the dimension of the vessel such that Equation [4] is exactly satisfied. Consequently, we obtained the optimum catheter size for a given vessel diameter such that the distributive model satisfies the lumped Equations (Equation [4] and [5]). In this way, we can generate a relationship between vessel diameter and catheter diameter such that the error in the CSA measurement is less than 5%. In one embodiment, different diameter catheters are prepackaged and labeled for optimal use in certain size vessel. For example, for vessel dimension in the range of 4-5 mm, 5-7 mm or 7-10 mm, our analysis shows that the optimum diameter catheters will be in the range of 0.91.4, 1.4-2 or 2-4.6 mm, respectively. The clinician can select the appropriate diameter catheter based on the estimated vessel diameter of interest. This decision will be made prior to the procedure and will serve to minimize the error in the determination of lumen CSA.

Percutaneous Valve and Valve Annulus Sizing

In addition to the foregoing, the disclosure of the present application discloses various devices, systems, and methods for sizing a percutaneous valve and/or a valve annulus and placing replacement valves within a luminal organ using a balloon.

Figure 8A:
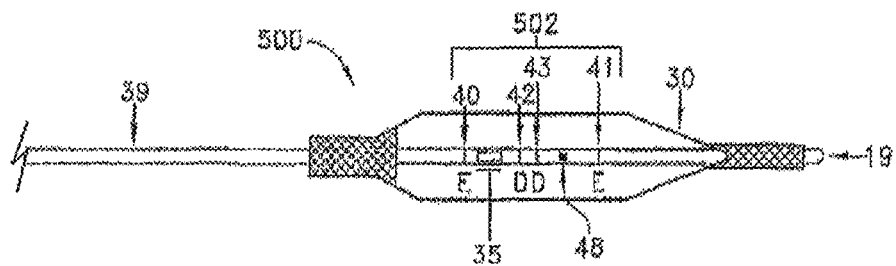
FIGS. 8A, 8B, and 8C show various embodiments of devices for sizing a percutaneous valve and/or a valve annulus, according to embodiments of the present disclosure.

An exemplary embodiment of a device for sizing a valve annulus 500 of the present disclosure is shown in FIG. 8A. As shown in FIG. 8A, an exemplary device 500 comprises a catheter 39 and a balloon 30 positioned thereon at or near the tip 19 (distal end) of catheter 39 so that any gas and/or fluid injected through catheter 20 into balloon 30 by way of a suction/infusion port 35 will not leak into a patient's body when such a device 500 is positioned therein.

Figure 8B:
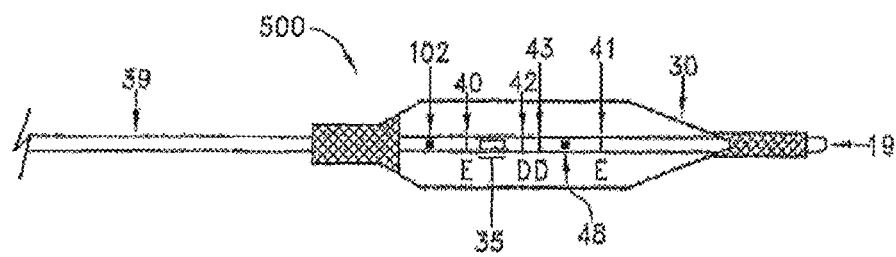

As shown in FIGS. 8A and 8B, device 500 comprises a detector 502, wherein detector 502, in at least one embodiment, comprises a tetrapolar arrangement of two excitation electrodes 40, 41 and two detection electrodes 42, 43 located inside balloon 30 for accurate determination of the balloon 30 cross-sectional area during sizing of a valve annulus. Such a tetrapolar arrangement (excitation, detection, detection, and excitation, in that order) as shown in FIG. 8A would allow sizing of the space within balloon 30, including the determination of balloon 30 cross-sectional area. As shown in FIG. 8A, device 500 comprises a catheter 39 (an exemplary elongated body), wherein balloon 30 is positioned thereon at or near the tip 19 (distal end) of catheter 39. In addition, an exemplary embodiment of a device 500, as shown in FIG. 8A, comprises a pressure transducer 48 capable of measuring the pressure of a gas and/or a liquid present within balloon 30. Device 500 also has a suction/infusion port 35 defined within catheter 39 inside balloon 30, whereby suction/infusion port 35 permits the injection of a gas and/or a fluid from a lumen of catheter 39 into balloon 30, and further permits the removal of a gas and/or a fluid from balloon 30 back into catheter 39.

Figure 8C:
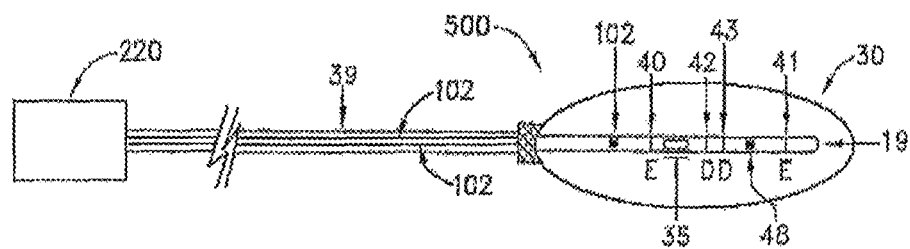

FIG. 8C, as referenced above, shows another exemplary embodiment of a device 500 of the present disclosure. FIG. 8C comprises several of the same components shown in the embodiments of a device 500 of the present disclosure shown in FIGS. 8A and 8B, but as shown in FIG. 8C, balloon 30 does not connect to catheter 39 at both relative ends of balloon 30. Instead, balloon 30 is coupled to catheter 39 proximal to electrodes 40, 41, 42, and 43, and is not coupled to catheter 39 distal to said electrodes. In addition, the exemplary embodiment of device 500 shown in FIG. 8C comprises a data acquisition and processing system 220 coupled thereto. The exemplary embodiments of devices 500 shown in FIGS. 8A and 8C are not intended to be the sole embodiments of said devices 500, as various devices 500 of the present disclosure may comprise additional components as shown in various other figures and described herein.

Figure 8D:
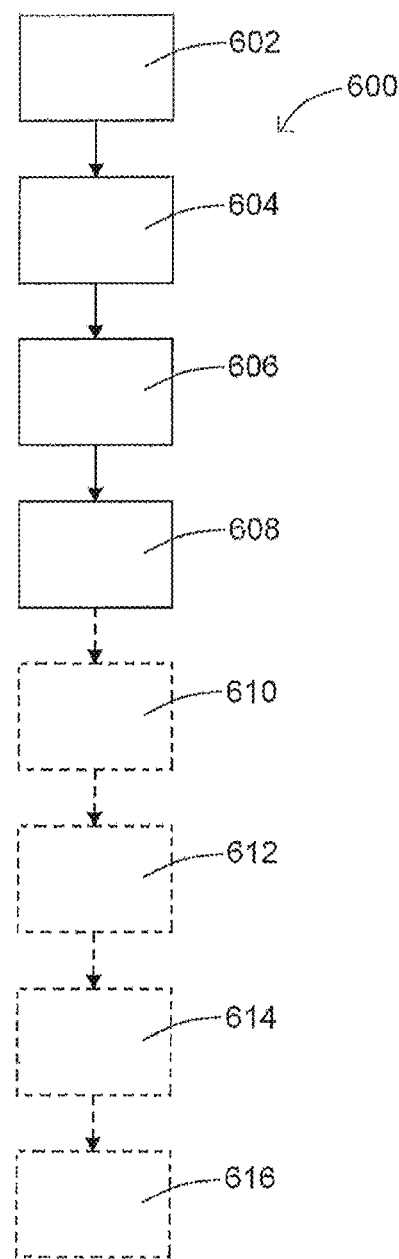
FIG. 8D shows steps of an exemplary method to size a percutaneous valve and/or a valve annulus, according to the present disclosure.

Various exemplary embodiments of devices 500 of the present disclosure may be used to size a valve annulus as follows. In at least one embodiment of a method to size a valve annulus of the present disclosure, method 600, as shown in FIG. 8D, comprises the steps of introducing at least part of a sizing device into a luminal organ at a valve annulus (an exemplary introduction step 602), wherein the sizing device 500 comprises a detector 502 and a pressure transducer 48 within a balloon 30 at or near a distal end 19 of sizing device 500. Method 600 then comprises the steps of inflating balloon 30 until a threshold pressure is detected by pressure transducer 48 within balloon 30 (an exemplary inflation step 604), and obtaining a first valve annulus measurement using detector 504 (an exemplary measurement step 606). In at least one embodiment, balloon 30 has a larger diameter than the valve annulus to be sized, so that when balloon 30 is initially inflated (inflation step 604), the diameter of balloon 30 will increase but the pressure of the balloon 30 will remain small because of excess balloon 30. Once the diameter of balloon 30 reaches the border of the annulus, the measured balloon pressure will begin to rise. In an exemplary inflation step 604, inflation step 604 comprises the step of introducing a fluid into a lumen of device 500, through a suction/infusion port 35, and into balloon 30. At the point of apposition (significant pressure rise, also referred to herein as a "threshold pressure"), the size of balloon 30 will correspond to the size of the annulus and hence the desired measurement. When a threshold pressure is reached within balloon 30, measurement step 606 may be performed to obtain an optimal first valve annulus measurement.

An exemplary measurement step 606 of method 600, in at least one embodiment, comprises measuring a balloon 30 cross-sectional area using detector 502. In an exemplary embodiment, measurement step 606 is performed when a threshold pressure is present within balloon 30. In at least one embodiment, the balloon 30 cross-sectional area is determined from a conductance measurement of a fluid present within balloon 30 obtained by detector 502, a known conductivity of the fluid, and a known distance between detection electrodes 41, 42.

Figure 9A:
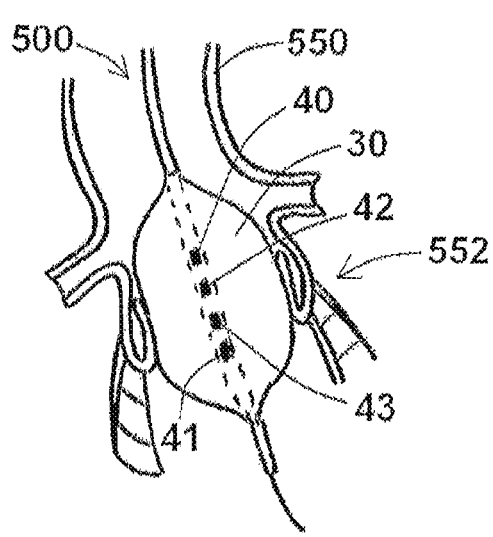
FIGS. 9A, 9B, and 9C show an exemplary embodiment of a sizing device of the present disclosure obtaining sizing data within a luminal organ (FIG. 9A), deflated but having a stent valve positioned around the device (FIG. 9B), and inflated to place the stent valve (FIG. 9C), according to embodiments of the present disclosure.

FIG. 9A shows an exemplary embodiment of a sizing device 500 positioned within a luminal organ 550 at a valve annulus 552. Device 500 is shown in FIG. 9A with an inflated balloon 30, with electrodes 40, 41, 42, 43 defined within the figure. At the time a threshold pressure within balloon 30 is identified by pressure transducer 48, electrodes 40, 41, 42, 43 (a detector 502 as referenced herein) may operate to obtain a first valve annulus measurement, such as a valve annulus cross-sectional area, corresponding to the cross-sectional area of balloon 30. Such a measurement (measurement step 606) is a more precise valve annulus measurement that can be obtained either visually (under fluoroscopy) or using pressure alone.

After measurement step 606 is performed, and in at least one embodiment of a method 600 of the present disclosure, method 600 further comprises the steps of withdrawing sizing device 500 from luminal organ 550 (an exemplary device withdrawal step 608). In an exemplary device withdrawal step 608, device withdrawal step 608 comprises the step of removing fluid from balloon 30, through suction/infusion port 35, and into the lumen of device 500, to deflate balloon 30. In at least one embodiment of method 600 comprises the optional steps of positioning a stent valve 560 (as shown in FIGS. 9B-9D) upon balloon 30 (an exemplary stent valve positioning step 610), reintroducing at least part of device 500 back into luminal organ 550 at valve annulus 552 (an exemplary reintroduction step 612), and reinflating balloon 30 to a desired inflation to place stent valve 560 within valve annulus 552 (an exemplary stent valve placement step 614).

Figure 9B:
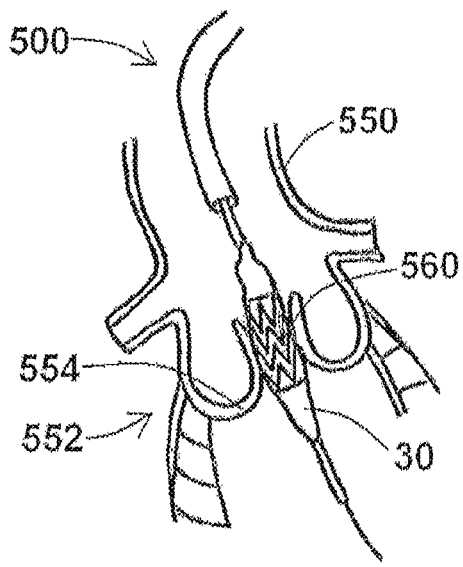
Figure 9C:
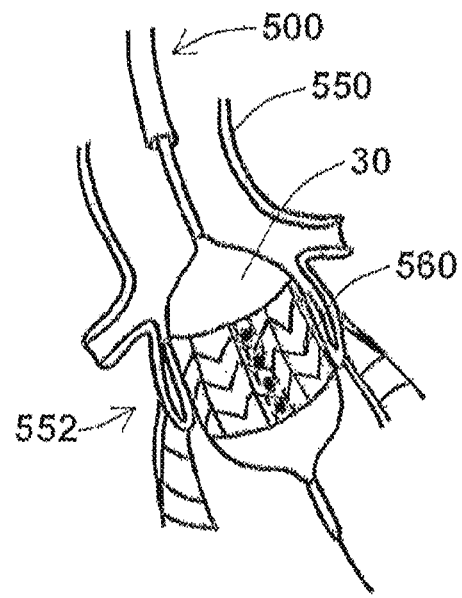
Figure 9D:
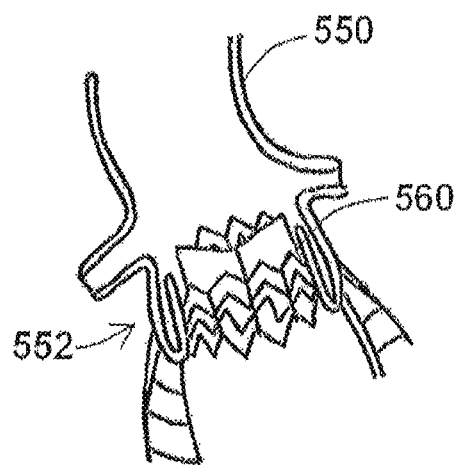
FIG. 9D shows a stent valve positioned within a luminal organ, according to an embodiment of the present disclosure.

At least some of the aforementioned steps of method 600 are also shown in FIGS. 9B-9D. As shown in FIG. 9B, and once the valve annulus has been sized using method 600 of the present disclosure, an appropriate size stent can then be placed within luminal organ 550. Detector 502, after a stent valve 560 has been positioned upon balloon 30, can then size balloon 30 carrying stent valve 560. FIG. 9B shows at least part of device 500 having stent valve 560 positioned upon a relatively or completely deflated balloon 30, and FIG. 9C shows the same device 500 having an inflated balloon 30 to place stent valve 560 within luminal organ 550. Balloon 30, as shown in FIG. 9C, is inflated until the desired size of stent valve 560 is reached to ensure the desired apposition. Since the wall thickness of balloon 30 is known, the size of balloon 30, when inflated, will reflect the size of stent valve 560. Device 500 can then be removed from luminal organ 550 (an exemplary device rewithdrawal step 616), wherein stent valve 560 remains positioned within luminal organ 550 at valve annulus 552.

FIG. 9B is also indicative of sizing a percutaneous valve 554 itself, whereby the percutaneous valve flaps are visible in FIG. 9B. Such sizing may be performed using an exemplary method 600 of the present disclosure, whereby an exemplary inflation step 604 comprises inflating balloon 30 at the site of percutaneous valve 554 until a threshold pressure is met, and whereby an exemplary measurement step 606 comprises obtaining a percutaneous valve opening measurement using detector 504.

Figure 10:
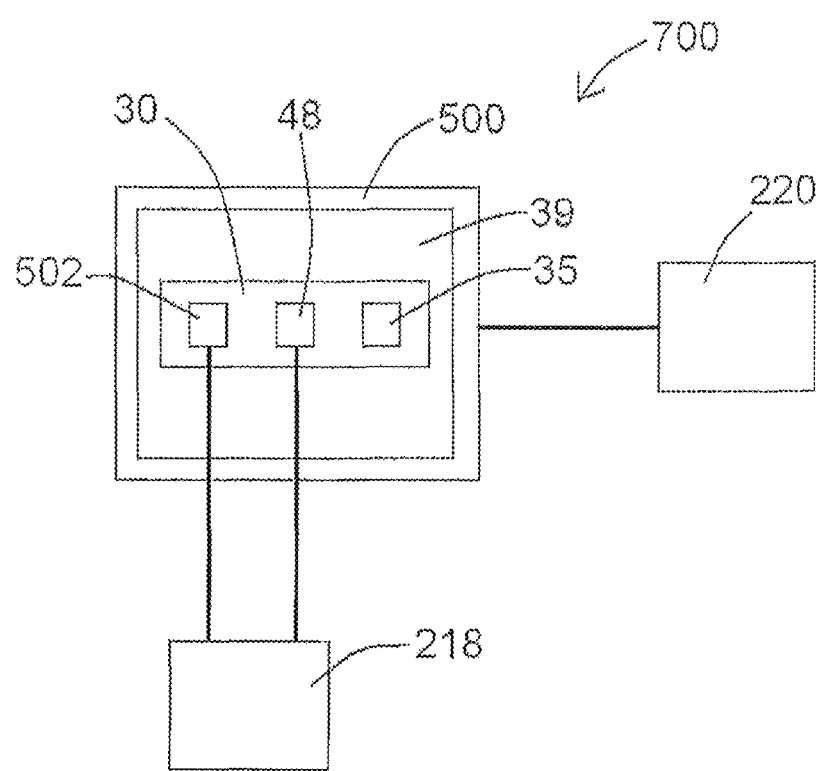
FIG. 10 shows a block diagram of an exemplary system for sizing a percutaneous valve and/or a valve annulus, according to an embodiment of the present disclosure.

An exemplary system for sizing a percutaneous valve and/or a valve annulus of the present disclosure is shown in the block diagram shown in FIG. 10. As shown in FIG. 10, system 700 comprises a device 500, a data acquisition and processing system 220 coupled thereto, and a current source 218 coupled to a detector 502 and a pressure transducer 48 of device 500. Device 500, as shown in FIG. 10, may comprise a catheter 39 (an exemplary elongated body) having a balloon 30 coupled thereto, wherein detector 502 and pressure transducer 48 are positioned along catheter 39 within balloon 30. A suction/infusion port 35 may also be defined within catheter 39, as referenced herein, to facilitate the movement of a fluid in and out of balloon 30 from catheter 39.

As referenced herein, a modified version of Ohm's law may be used, namely:

$$CSA = (G/L)/\alpha \quad [14]$$

wherein CSA is the cross-sectional area of balloon 30, G is the electrical conductance given by a ratio of current and voltage drop (I/V, wherein I represents injected current and V is the measured voltage drop along detection electrodes 41, 42), L is a constant for the length of spacing between detection electrodes 41, 42 of sizing device 500, and $\alpha$ is the electrical conductivity of the fluid within balloon 30. Equation [14] can then be used to provide CSA in real time given the conductivity of fluid used to inflate the balloon (such as, for example, half normal saline (0.9% NaCl)) and half contrast (iodine, etc.), the measure conductance (G) and the known distance L.

Figure 11:
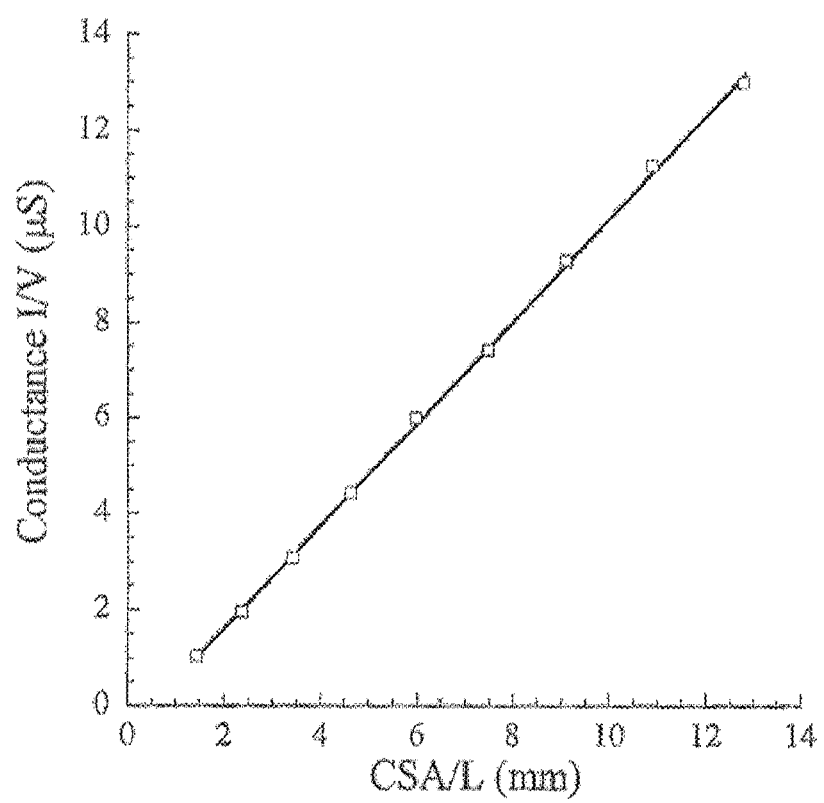
FIG. 11 shows calibration data of an exemplary sizing device using phantoms having known cross-sectional areas, according to an embodiment of the present disclosure.

A typical calibration curve of an impedance balloon 30 is shown in FIG. 11. As shown in FIG. 11, the slope of the line provides the conductivity ($\alpha$) of fluid within balloon. The solid line shown in FIG. 11 has a linear fit of the form $y=1.00664 \times x - 0.4863$, wherein $R^2=0.99$. Calibration, in at least this example, was performed using various phantoms having known CSAs.

The present disclosure also includes disclosure of devices, systems, and methods to size various luminal organs and openings or apertures within luminal organs, including, but not limited to, renal artery sizing. Renal arteries, as well as various other luminal organs, can have different dimensions (diameters, cross-sectional areas, etc.) from patient to patient, and use of various balloon 30 embodiments may be chosen depending on the sizing procedure and/or treatment procedure performed. Furthermore, various openings or apertures within luminal organs can be more or less compliant or rigid that others, and an understanding or knowledge of the relative compliance or rigidity may impact a potential course of patient treatment or care.

The present disclosure includes significant disclosure regarding sizing of luminal organs using impedance by obtaining conductance data and using said data to obtain luminal organ parameters such as cross-sectional area and diameter. Additional disclosure is provided above regarding obtaining similar data within a valve annulus, an exemplary opening or aperture (as described in further detail below) within a luminal organ. As such, the present disclosure includes disclosure of devices, systems, and methods to obtain conductance data useful to determine luminal organ opening or aperture 1310 information, such as diameters and/or cross-sectional areas.

Devices 500 and systems 700 of the present disclosure include balloons 30 having various impedance sensors (an exemplary detector 502, as previously referenced herein, such as devices comprising electrodes 40, 41, 42, and 43 (whereby electrodes 40 and 41 are excitation electrodes and electrodes 42 and 43 are detection electrodes), comprising electrodes 25, 26, 27, and 28 (whereby electrodes 25 and 28 are excitation electrodes and electrodes 26 and 27 are detection electrodes), and/or comprising electrodes 51, 52, 53, 54, 55, 56, and 57 (whereby electrodes 51 and 57 are excitation electrodes and electrodes 52, 53, 54, 55, and 56 are detection electrodes), for example, positioned on and/or within a surface 1200 of balloon 30. FIG. 12 shows an exemplary device 500 embodiment, identifying detector 502 as comprising electrodes 40, 41, 42, 43, by way of example. Balloon 30 can be coupled to catheter 20, 21, 22, or 39, as referenced herein, with catheter 20 being the exemplary catheter shown in FIG. 12. Various wires 1202, as shown in FIG. 12, can be used to connect the various electrodes 40, 41, 42, and 43 (or other electrodes as referenced herein) to, for example, a data acquisition and processing system 100 or 220 as referenced herein.

Said electrodes 40, 41, 42, and 43, when operated consistent with the present disclosure, can be used to indicate whether or not a balloon 30 has inflated to the extent of making physical contact with a wall 1300 of a luminal organ 150 (such as a blood vessel, heart, or other luminal organ of the present disclosure) For example, conductance measurements obtained using electrodes 40, 41, 42, 43 while balloon 30 is not in contact with wall 1300 of luminal organ will differ from conductance measurements obtained using the same electrodes 40, 41, 42, 43 while balloon 30 is in contact with wall 1300 of luminal organ 150, such as when one or more of electrodes 40, 41, 42, 43 contact wall 1300.

Renal artery sizing, for example, can factor into an appropriate treatment/procedure to treat hypertension using renal ablation. Surgical approaches have been shown to be effective, but they are of course traumatic, noting that an intravascular approach would be preferred. Various embodiments of devices 500 of the present disclosure can be used to obtain accurate sizing information (diameter and/or cross-sectional area) of renal arteries, and in some embodiments, the same devices 500 can be used for ablation. For example, FIG. 12 shows a device 500 embodiment having an ablation contact 1250 positioned on and/or within a surface 1200 of balloon 30. Operation of ablation contact 1250 can also be controlled using data acquisition and processing system 220, with ablation contact 1250 being powered via wire 1202. As referenced above, balloon 30 can be inflated to the point where it is known that balloon 30 is contacting a vessel wall 150. Ablation contact 1250 can then be operated to perform renal ablation, for example, to treat hypertension. Conversely, devices 500 without ablation contacts 1250 can be used to provide sizing information, while other ablation devices known or developed in the medical arts can perform the ablation. As such, the present disclosure includes disclosure of devices, systems, and methods to perform renal ablation and to treat hypertension.

Intraseptal ventricular defect (ISD) is a congenital heart defect where the septum of the heart is not completely formed. Determining whether or not the septum is rigid or compliant can be an important indicator as to the potential treatment of said defect, as a more compliant septum can be treated differently as compared to a more rigid septum.

Figure 14:
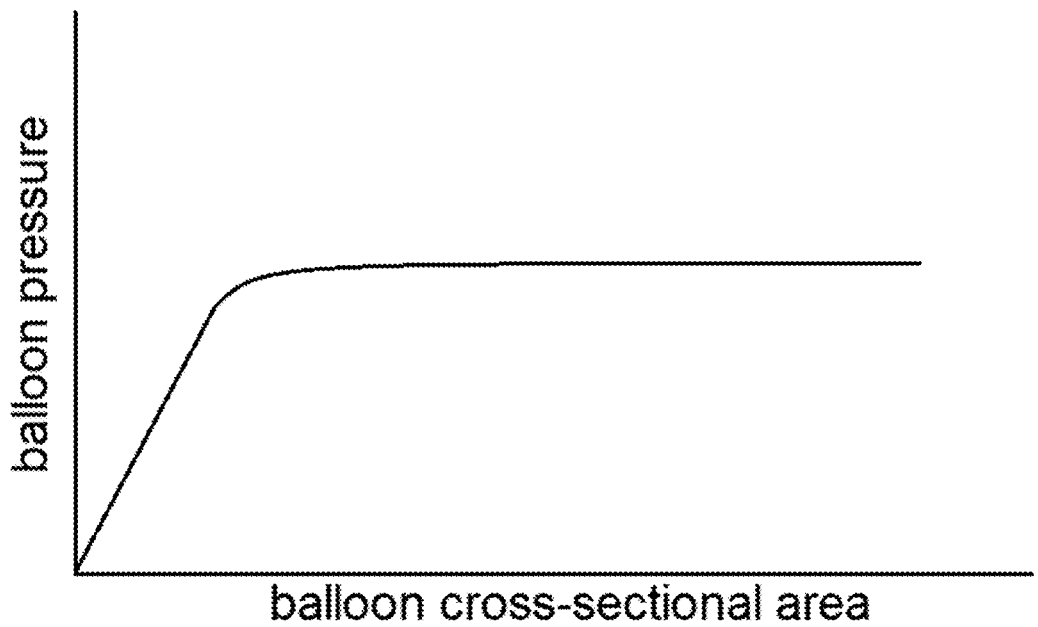
FIG. 14 shows a graph of pressure versus balloon cross-sectional area indicative of sizing of a rigid or relatively rigid luminal organ aperture or opening, according to the present disclosure.

In at least one method of obtaining a size parameter of a luminal organ opening or aperture 1310, such as a septum of the heart, a balloon 30 of a device 500 of the present disclosure is positioned within said opening or aperture 1310, such as shown in FIG. 13. Balloon 30, in such a device 500 embodiment, would comprise a compliant balloon 30. Should said opening or aperture 1310 (referring to the luminal organ at the opening or aperture and/or adjacent tissue forming the opening or aperture) be rigid or relatively rigid, inflation of balloon 30 and obtaining various conductance measurements (used to determine a luminal organ parameter, such as diameter or cross-sectional area as referenced herein), would result in a series of measurements whereby a) inflation of balloon 30 prior to balloon 30 contacting a luminal organ 150 wall 1300 within said opening or aperture would identify increasingly larger cross-sectional areas (corresponding to increasing larger cross-sectional areas of balloon 30), and b) when balloon 30 is inflated to the point of contacting said wall 1300, additional conductance measurements (used to determine a luminal organ parameter, such as diameter or cross-sectional area as referenced herein) would generally result in a consistent/steady cross-sectional area measurement, as the rigid or relatively rigid opening or aperture 1310 would prevent further balloon 30 distension within said opening or aperture 1310. This is generally depicted in FIG. 14, noting that an absolute size (cross-sectional area) of opening or aperture 1310 can be obtained.

Figure 15:
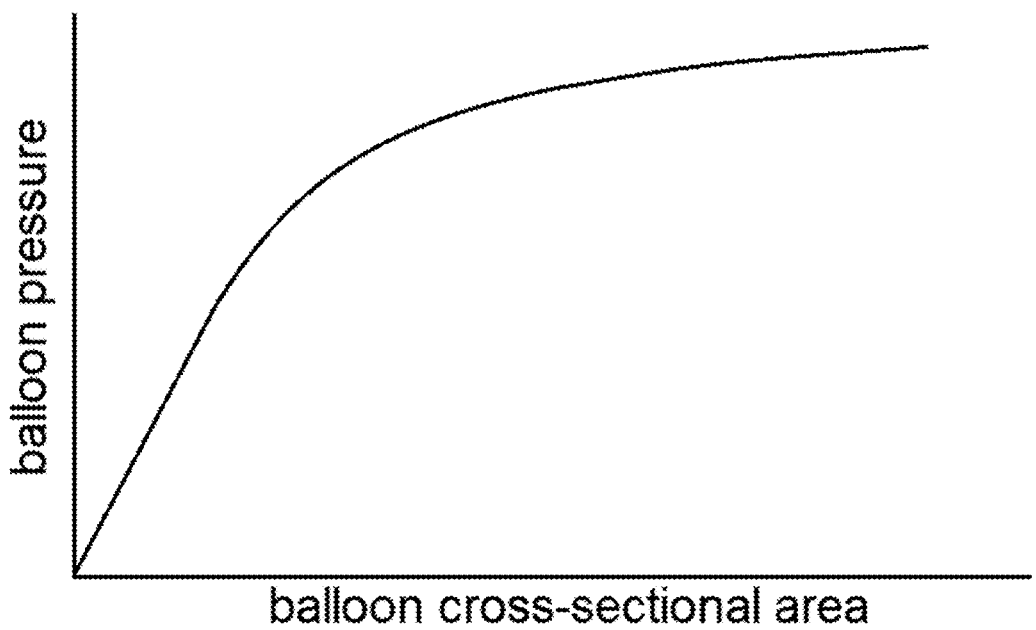
FIG. 15 shows a graph of pressure versus balloon cross-sectional area indicative of sizing of a compliant or relatively compliant luminal organ aperture or opening, according to the present disclosure.

Conversely, and should opening or aperture 1310 be compliant or relatively compliant, inflation of balloon 30 and obtaining various conductance measurements (used to determine a luminal organ parameter, such as diameter or cross-sectional area as referenced herein), would also result in a series of measurements whereby inflation of balloon 30 prior to balloon 30 contacting a luminal organ 150 wall 1300 within said opening or aperture 1310 would identify increasingly larger cross-sectional areas (corresponding to increasing larger cross-sectional areas of balloon 30). However, when balloon 30 is inflated to the point of contacting said wall 1300, additional conductance measurements (used to determine a luminal organ parameter, such as diameter or cross-sectional area as referenced herein) would continue to identify larger cross-sectional areas, for example, but would do so at a lesser rate, and would ultimately taper off, indicating that said opening or aperture 1310 has stretched to its general limit based upon balloon inflation. This is generally depicted in FIG. 15. As such, the present disclosure includes disclosure of devices, systems, and methods to obtain sizing and/or compliance data regarding a luminal organ 150 opening or aperture 1310, useful, for example, to treat a septal defect, such as an intraseptal ventricular defect.

The present disclosure also includes disclosure of various other openings of luminal organs, including, but not limited to, the opening of an atrial appendage (such as a left atrial appendage (LAA) or a right atrial appendage (RAA)), as well as sizing the LAA or RAA itself.

Figure 16:
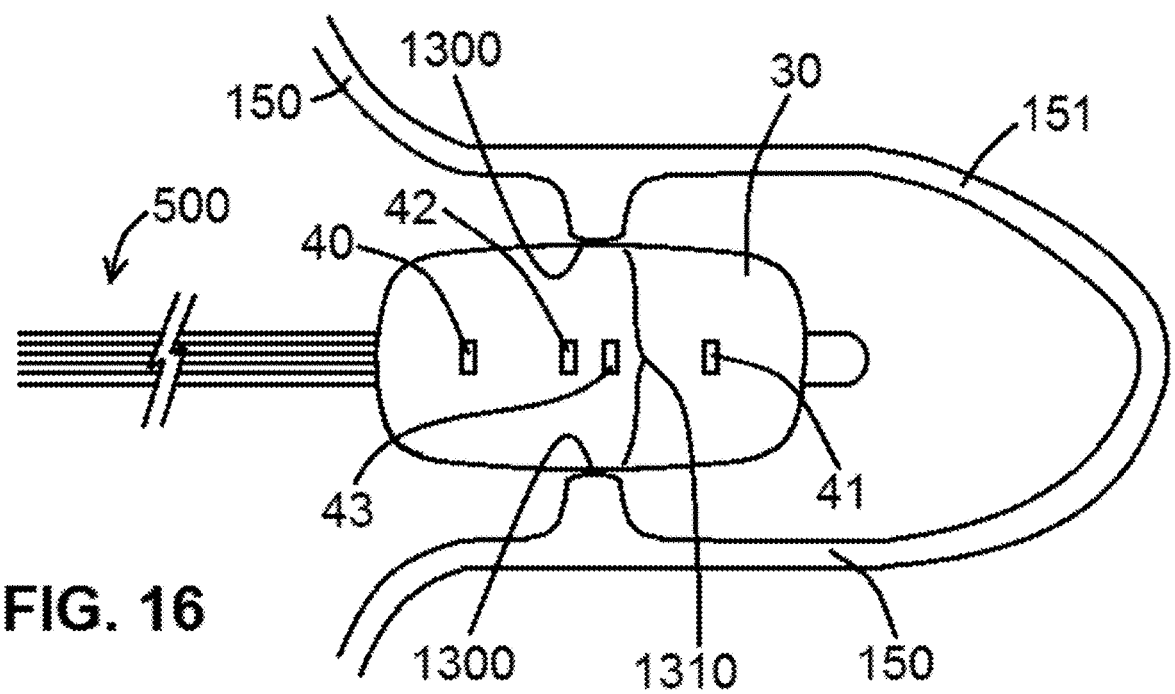
FIG. 16 shows a side view of a device for sizing a luminal organ or sizing an opening or aperture of a luminal organ at an atrial appendage (namely the opening of the atrial appendage), according to the present disclosure.

In at least one method of obtaining a size parameter of a luminal organ opening or aperture 1310, such as the opening or aperture 1310 of a an atrial appendage 151 (such as a left atrial appendage or a right atrial appendage), a balloon 30 of a device 500 of the present disclosure is positioned within said opening or aperture 1310, such as shown in FIG. 16, wherein the luminal organ 150 comprises a heart having an atrial appendage 151. Balloon 30, in such a device 500 embodiment, would comprise a compliant balloon 30. Should said opening or aperture 1310 (referring to the luminal organ 150 at the opening or aperture 1310 of the atrial appendage 151) be rigid or relatively rigid, inflation of balloon 30 and obtaining various conductance measurements (used to determine a luminal organ parameter, such as diameter or cross-sectional area as referenced herein), would result in a series of measurements whereby a) inflation of balloon 30 prior to balloon 30 contacting a luminal organ 150 wall 1300 within said opening or aperture 1310 would identify increasingly larger cross-sectional areas (corresponding to increasing larger cross-sectional areas of balloon 30), and b) when balloon 30 is inflated to the point of contacting said wall 1300, additional conductance measurements (used to determine a luminal organ parameter, such as diameter or cross-sectional area as referenced herein) would generally result in a consistent/steady cross-sectional area measurement, as the rigid or relatively rigid opening or aperture 1310 would prevent further balloon 30 distension within said opening or aperture 1310. This is generally depicted in FIG. 14, noting that an absolute size (cross-sectional area) of opening or aperture 1310 can be obtained. In such an embodiment, an absolute size (cross-sectional area) of an opening or aperture 1310 of an atrial appendage 151 can be obtained using an exemplary system 700 or device 500 of the present disclosure. Furthermore, the opening or aperture 1310 of the atrial appendage 151 can be sized using any number of devices, systems, and or methods of the present disclosure as referenced herein.

Figure 17:
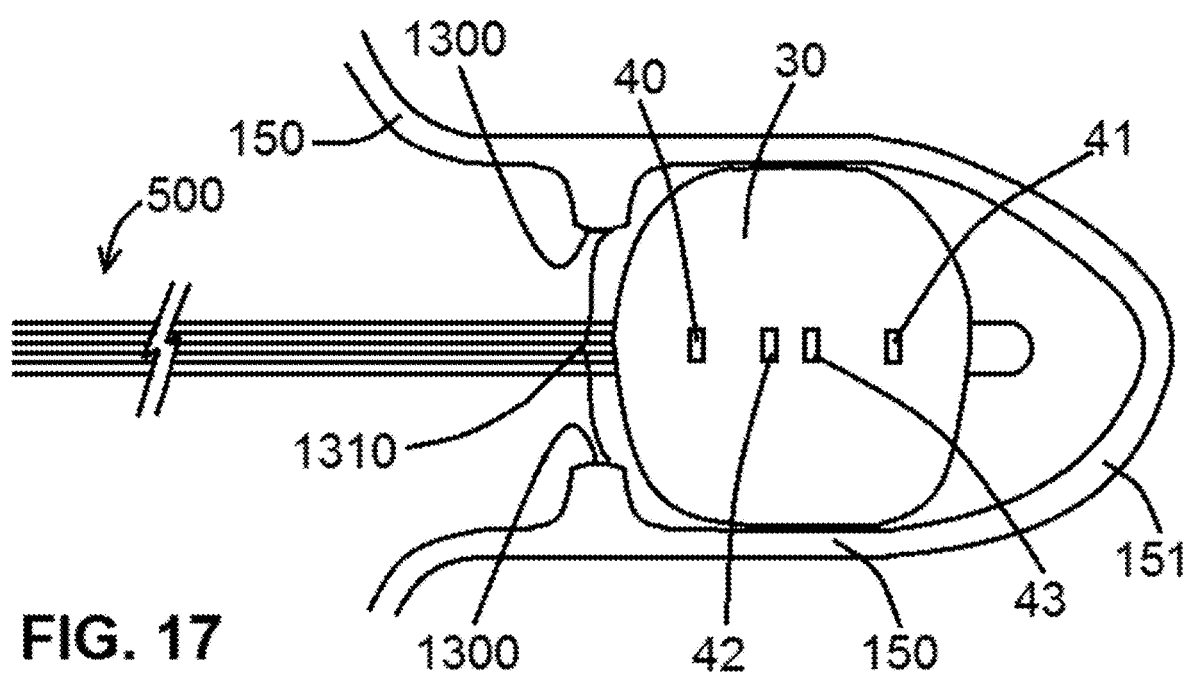
FIG. 17 shows a device for sizing an atrial appendage whereby the balloon is positioned within the atrial appendage, according to the present disclosure.

In at least one method of obtaining a size parameter of a luminal organ opening or aperture 1310, such as an atrial appendage 151 itself, a balloon 30 of a device 500 of the present disclosure is positioned within the atrial appendage 151 itself, such as shown in FIG. 17. Balloon 30, in such a device 500 embodiment, would comprise a compliant balloon 30. Should the atrial appendage 151 be rigid or relatively rigid, inflation of balloon 30 and obtaining various conductance measurements (used to determine a luminal organ parameter, such as diameter or cross-sectional area as referenced herein), would result in a series of measurements whereby a) inflation of balloon 30 prior to balloon 30 contacting a luminal organ 150 wall 1300 within the atrial appendage 151 would identify increasingly larger cross-sectional areas (corresponding to increasing larger cross-sectional areas of balloon 30), and b) when balloon 30 is inflated to the point of contacting said wall 1300 of the atrial appendage 151, additional conductance measurements (used to determine a luminal organ parameter, such as diameter or cross-sectional area as referenced herein) would generally result in a consistent/steady cross-sectional area measurement, as the rigid or relatively rigid atrial appendage 151 would prevent further balloon 30 distension within said atrial appendage 151. This is generally depicted in FIG. 14, noting that an absolute size (cross-sectional area) of the atrial appendage 151 can be obtained. In such an embodiment, an absolute size (cross-sectional area) of an atrial appendage 151 itself can be obtained using an exemplary system 700 or device 500 of the present disclosure. Furthermore, and as an atrial appendage 151 is an exemplary luminal organ 150 of the present disclosure, the atrial appendage 151 can be sized using any number of devices, systems, and or methods of the present disclosure as referenced herein.

Figure 18:
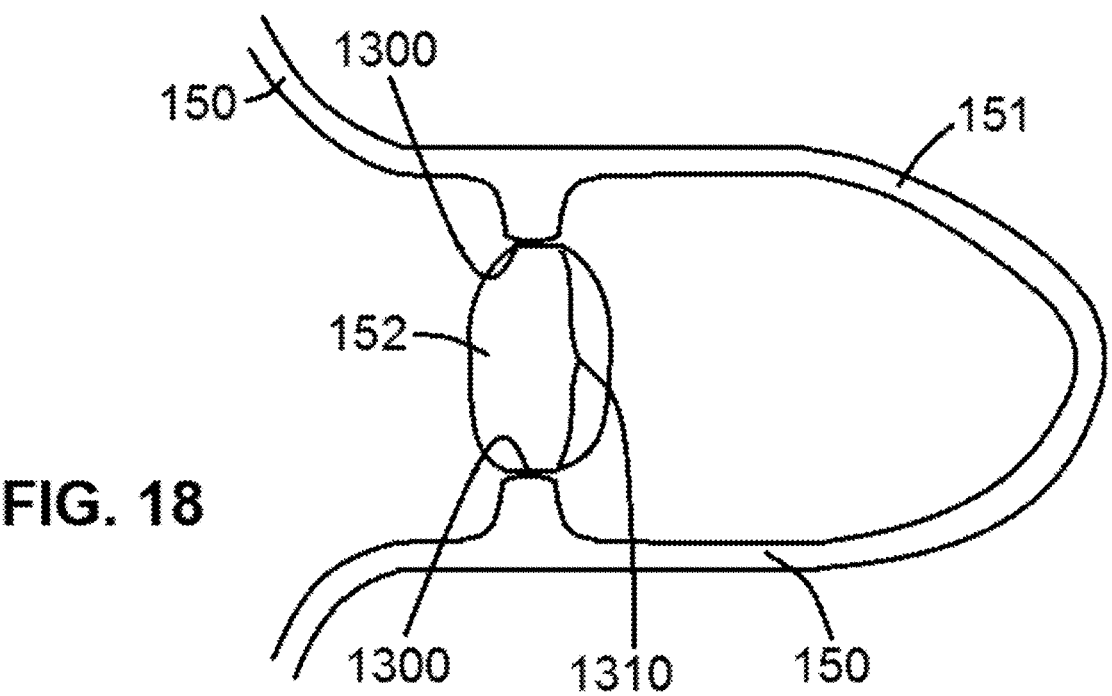
FIG. 18 shows an occluder positioned within an opening or aperture of a luminal organ at an atrial appendage (namely the opening of the atrial appendage) so to occlude the same, according to the present disclosure.
Figure 19:
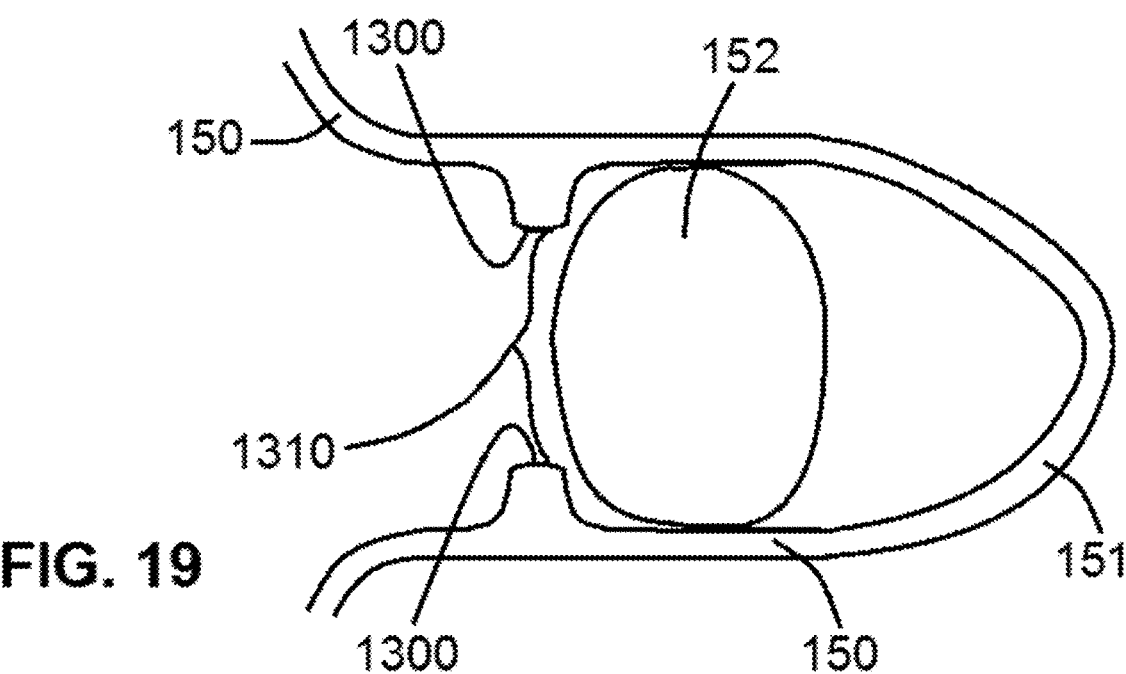
FIG. 19 shows an occluder positioned within an atrial appendage so to occlude the same, according to the present disclosure.

Sizing of the atrial appendage 151 or an opening or aperture 1310 of the atrial appendage 151 can be performed so that an occluder 152 of a desired size can be positioned at the opening or aperture 1310 of the atrial appendage 151, such as shown in FIG. 18, or within the atrial appendage 151 itself, such as shown in FIG. 19. By obtaining size data of the opening or aperture 1310 of the atrial appendage 151 and/or the atrial appendage itself, an occluder 152 of an appropriate and safe size can be selected for insertion into the said opening or aperture 1310 or said atrial appendage 151. By using an appropriately-sized occluder 152, the opening or aperture 1310 of the atrial appendage 151 or said atrial appendage 151 itself can be effectively occluded without exerting unnecessary force against said opening or aperture 1310 of the atrial appendage 151 or said atrial appendage 151 itself, which could potentially cause rupture of the atrial appendage 151.

Such embodiments of devices 500 of the present disclosure have several advantages. First, electrodes 40, 41, 42, and 43 are positioned along catheter 39 within balloon 30, so minimal risk to damage of said electrodes arises. Second, and since balloon 30 insulates the electric field generated by excitation electrodes 40, 41, there is no parallel conductance and hence no need for two injections to obtain a desired measurement. In addition, said devices 500 incorporate the ability to size a valve and/or a valve annulus and can also deliver a stent valve 560 as referenced herein. Using Equation [14] for example, real-time measurements of CSA can be obtained as desired, with no additional procedures required by a physician. The sizing results are quite accurate (as shown in FIG. 11), providing additional confidence of the sizing measurements without the need for echocardiograms, MRIs, or other expensive imaging mechanisms.

The present disclosure includes disclosure of a novel sizing valvuloplasty conductance balloon catheter system, such as sizing devices 500 of the present disclosure including those shown in FIGS. 9A-9D and otherwise referenced herein, that serve as a universal balloon (balloon 30) for valve sizing prior to implant (TAVR, TMVR, etc.), such as the implantation of a stent valve 560 as referenced herein. The present disclosure further discloses the use of this technology to accurately measure and display real-time left ventricular outflow tract (LVOT) obstruction during mitral valve (valve device 560, for example) implant delivery. Such a use would allow LVOT reduction to be assessed during TMVR since a sizing profile can be obtained in real-time and any external pinching on the LVOT balloon can be detected as a decrease in LVOT annular profile. This would be extremely useful in TMVR to diagnose/prevent LVOT obstruction.

Figure 20A:
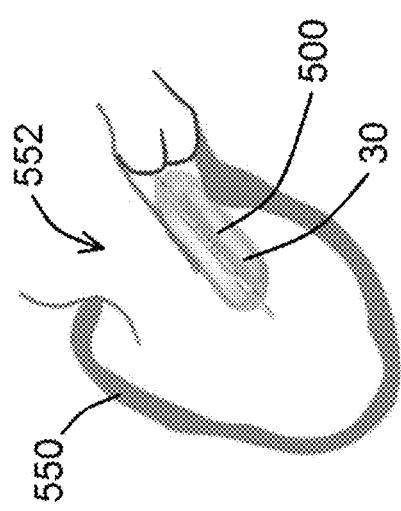
FIG. 20A shows a sizing device positioned adjacent to a valve annulus or opening, according to the present disclosure.
Figure 20B:
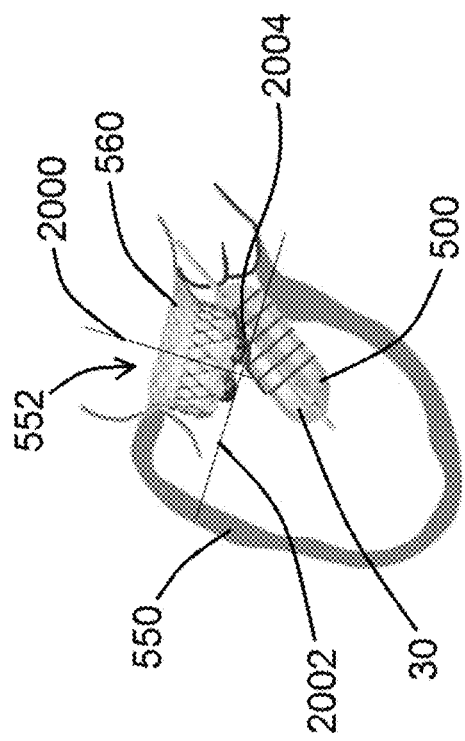
FIGS. 20B and 20C shows a sizing device positioned adjacent to a valve annulus or opening and a valve device positioned at the valve annulus or opening, according to the present disclosure.
Figure 20C:
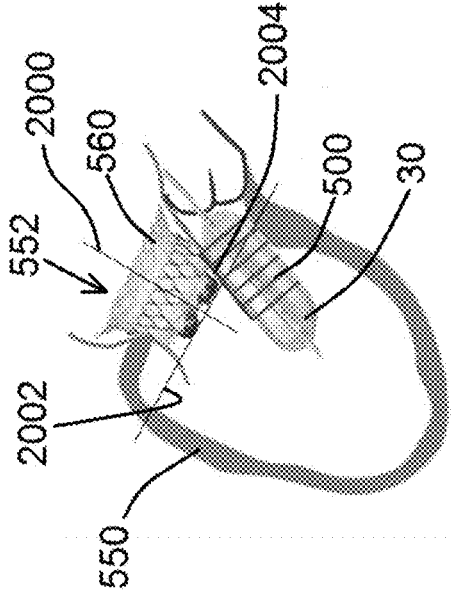
Figure 20D:
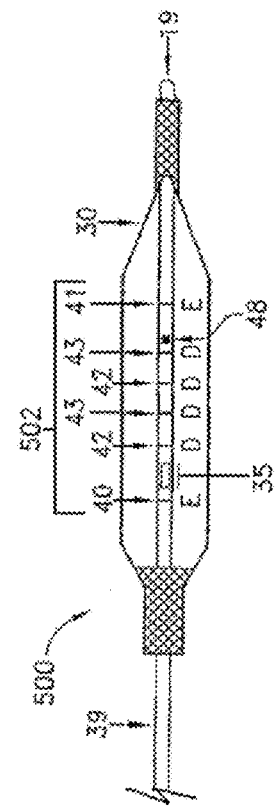
FIG. 20D shows a distal portion of a sizing device, according to the present disclosure.

Current TMVR procedures already invoke an arterial access through a 6 Fr. sheath which would accommodate our sizing device 500. In one embodiment, such as shown in FIGS. 20A, 20B, and 20C, a 6Fr compatible valvuloplasty sizing device 500 can be used, with multiple detection electrodes 42, 43 (whereby electrodes 42 and 43 represent detection electrodes that can be used in various multiples of one another), such as at 0.5 cm intervals or other intervals as may be desired, and using one set/pair of excitation electrodes 40, 41. The diameter of the sizing balloon 30, in such an embodiment, will accommodate 23-25 mm with length of balloon 30 in the range of 4-6 cm. FIG. 20D shows a distal portion of an exemplary sizing device, FIG. 20A shows a sizing device 500, such as referenced above and otherwise herein, positioned adjacent to a valve annulus or opening 552 of a luminal organ 550. FIGS. 20B and 20C show the sizing device 500, with balloon 30 inflated, positioned at the same location as noted in FIG. 20A, but now with a valve device 560 positioned within the valve annulus or opening 552, with valve device at a relatively larger expansion configuration in FIG. 20B as compared to FIG. 20C. Sizing device 500, when operated to obtain size measurements using impedance, as referenced herein (cross-sectional area, diameter, etc., of balloon 30, corresponding to the general boundary of balloon 30 formed by the luminal organ 550 at the location of balloon 30 (such as at the location of valve annulus or opening 552 or adjacent thereto)), can create a real-time sizing profile (namely sizing data over time), and any external pinching on the LVOT balloon can be detected as a decrease in LVOT annular profile. FIG. 20D shows a distal portion of an exemplary sizing device of the present disclosure, with features/components as referenced herein.

Desired alignment or general positioning of valve device 560 within valve annulus or opening 552 can also be performed/achieved with respect to the foregoing. As shown in FIG. 20B, an axis of fluid flow 2000 though valve device 560 corresponding to positioning of valve device 560 within the valve annulus or opening 552 is not proper, as compared to FIG. 20C, whereby the axis of fluid flow 2000 though valve device 560 corresponding to positioning of valve device 560 within the valve annulus or opening 552 is proper (as indicative of perpendicular axis 2002, which is perpendicular to axis of fluid flow 2000), as desired alignment or positioning of valve device 560 would result in valve device 560 being aligned with perpendicular axis 2002, as shown in FIG. 20C, as may be desired. It is understood that a valve device 560 may not have a specific alignment axis, but in certain instances, such as shown in FIGS. 20B and 20C, a valve device 560 may need or require a proper alignment or placement, such as shown in FIG. 20C, as compared to that as shown in FIG. 20B. Perpendicular axis 2002 can generally correspond to a valve annulus or opening 552, whereby axis 2002 aligns with valve annulus or opening 552 as shown in FIG. 20C, but does not so align as shown in FIG. 20B.

Furthermore, and as shown in FIGS. 20B and 20C, a potential or actual contact location 2004 can or may exist between valve device 560 and sizing device 500. As shown in FIG. 20B, contact location 2004 is an actual contact location (or a relatively higher degree of contact) between valve device 560 and sizing device 500, whereby valve device 560 contacts sizing device 500 when balloon 30 of sizing device 500 is inflated, which can be indicative of improper alignment or positioning of valve device 560 within valve annulus or opening 552. Conversely, and as shown in FIG. 20C, contact location 2004 is a potential contact location (or a relatively lower degree of contact as compared to that shown in FIG. 20B) between valve device 560 and sizing device 500, whereby valve device 560 either does not contact sizing device 500 or contacts sizing device 500 when balloon 30 of sizing device 500 is inflated, which can be indicative of proper alignment or positioning of valve device 560 within valve annulus or opening 552.

In view of the same, the present disclosure includes disclosure of methods to assess LVOT reduction during a valve replacement procedure, detected as a decrease in an annular profile, corresponding to size data obtained using sizing device 500.

In addition to the foregoing, the present disclosure also includes disclosure relating to sensing the obstruction, such as by sensing the obstruction using a pressure sensor (an exemplary pressure transducer 48 of the present disclosure, such as shown in FIG. 20D) internal to the balloon 30 of sizing device 500. For example, a detected pressure would increase if a transcatheter mitral implant would impinge on the balloon, whereby squeezing (or otherwise applying pressure to the outside of the balloon) would compress a fluid within the balloon and increase the pressure. So, as referenced above, impedance can be used to obtain sizing data (such as by using a detector 502 of a sizing device 500 having multiple electrodes 40, 41, 42, 43, for example), which can be used to create a sizing profile and indicate whether or not a valve device 560 (such as a transcatheter mitral implant or other devices referenced herein) is impinging balloon 30 of sizing device 500, and pressure, such as by way of detected changes in pressure within balloon 30, can also be an indication of whether or not valve device 560 impinges balloon 30. In view of the same, the present disclosure includes disclosure of a device (such as a sizing device 500), which may or may not include electrodes 40, 41, 42, 43, but does contain a pressure transducer 48 within a balloon 30, so that changes in pressure, such as by way of impingement of balloon 30 by a valve device 560, can be detected over time (such as by way of generating a profile of pressures over time and detecting changes in pressure during placement of valve device 560 within the body, so that proper placement and/or alignment of valve device 560 can be achieved, as discussed above. Undesired pressure applied to the outside of balloon 30, detected by pressure transducer 48, can indicate improper placement and/or alignment of valve device 560 within the body.

Again, it is noted that the various devices, systems, and methods described herein can be applied to any body lumen or treatment site. For example, the devices, systems, and methods described herein can be applied to any one of the following exemplary bodily hollow organs: the cardiovascular system including the heart, the digestive system, the respiratory system, the reproductive system, and the urogenital tract.

While various embodiments of devices, systems, and methods for measuring a luminal organ opening or aperture using a balloon sizing device have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A method, comprising:
   introducing a sizing device comprising a balloon configured for inflation into a luminal organ so that the balloon is adjacent to a valve annulus or opening;
   introducing a valve device separate from the sizing guide within the valve annulus or opening, adjacent the balloon;
   moving the valve device within the valve annulus or opening;
   operating the system sizing device to obtain measurements of the balloon over time during the step of moving the valve device within the valve annulus or opening; and
   generating a real-time measurement profile of the measurements over time.

2. The method of claim 1, wherein the method is performed to assess left ventricular outflow tract (LVOT) reduction during a valve replacement procedure.

3. The method of claim 1, wherein the measurements are size measurements, and wherein the method is performed to produce accurate mitral annular sizing measurements.

4. The method of claim 1, further comprising the step of:
   obtaining at least one initial measurement of the balloon when adjacent to the valve annulus or opening prior to the step of introducing the valve device within the valve annulus or opening, the at least one initial measurement selected from the group consisting of an initial sizing measurement and an initial pressure measurement.

5. The method of claim 1, wherein the real-time measurement profile can indicate external pinching of the balloon from the valve device when the real-time measurement profile indicates a decrease in size of the balloon.

6. The method of claim 1, wherein an axis of fluid flow through the valve annulus or opening is defined as an optimal axis of flow, and wherein the step of moving the valve device is performed to align the device along and consistent with a perpendicular axis that is perpendicular to the axis of fluid flow, wherein the perpendicular axis corresponds to an axis of the valve annulus or opening.

7. The method of claim 6, wherein when the step of moving the valve device causes an increase in pressure within the balloon, which is indicative of improper alignment of the valve device within the valve annulus or opening.

8. The method of claim 7, wherein the increase in pressure is determined using a pressure sensor or pressure transducer positioned within the balloon.

9. The method of claim 6, wherein the measurements are pressure measurements, wherein when the step of moving the valve devices causes a change in pressure within the balloon, and wherein a relative lowest pressure within the balloon is indicative of proper alignment of the valve device within the valve annulus or opening.

10. The method of claim 1, wherein the real-time sizing profile corresponds to a degree of left ventricular outflow tract (LVOT) obstruction over time.

11. The method of claim 1, wherein the measurements comprise size measurements, wherein the sizing device further comprises at least two detection electrodes positioned in between two excitation electrodes, wherein excitation of the two excitation electrodes permits impedance measurements to be obtained within the balloon, and wherein the impedance measurements correspond to the size measurements.

12. The method of claim 1, wherein the measurements comprise pressure measurements, wherein the real-time measurement profile comprises a real-time pressure measurement profile, wherein the sizing device further comprises a pressure sensor or pressure transducer positioned within the balloon, and wherein the step of generating the real-time measurement profile is performed to generate the real-time pressure measurement profile.

13. The method of claim 1, wherein the sizing device further comprises at least two detection electrodes positioned in between two excitation electrodes, wherein the sizing device does not comprise a pressure sensor or pressure transducer, and wherein the step of operating the sizing device is performed to obtain the measurements corresponding to size measurements of the balloon over time.

14. The method of claim 1, wherein the sizing device further comprises a pressure sensor or pressure transducer positioned within the balloon, wherein the sizing device does not comprise any excitation electrodes or any detection electrodes, and wherein the step of operating the sizing device is performed to obtain the measurements corresponding to pressure measurements within the balloon over time.

15. The method of claim 1, wherein the sizing device further comprises at least two detection electrodes positioned in between two excitation electrodes, wherein the sizing device further comprises a pressure sensor or pressure transducer positioned within the balloon, and wherein the step of operating the sizing device is performed to obtain the measurements corresponding to size measurements of the balloon over time and pressure measurements within the balloon over time.

* * * * *